United States Patent
Lee et al.

(10) Patent No.: US 10,864,232 B2
(45) Date of Patent: Dec. 15, 2020

(54) MODIFIED NATURAL KILLER T CELLS, PHARMACEUTICAL COMPOSITIONS AND USES THEREOF

(71) Applicant: FULLHOPE BIOMEDICAL CO., LTD., New Taipei (TW)

(72) Inventors: Jan-Mou Lee, New Taipei (TW); Chih-Hao Fang, New Taipei (TW); Ya-Fang Cheng, New Taipei (TW); Da-Tsen Wei, New Taipei (TW); Kai-Yuan Jhou, New Taipei (TW)

(73) Assignee: FULLHOPE BIOMEDICAL CO., LTD., New Taipiei (TW)

( * ) Notice: Subject to any disclaimer, the term of this patent is extended or adjusted under 35 U.S.C. 154(b) by 496 days.

(21) Appl. No.: 15/091,975

(22) Filed: Apr. 6, 2016

(65) Prior Publication Data
US 2016/0296564 A1  Oct. 13, 2016

Related U.S. Application Data

(60) Provisional application No. 62/144,066, filed on Apr. 7, 2015.

(51) Int. Cl.
| | | |
|---|---|---|
| *A61K 35/17* | (2015.01) | |
| *C12N 5/0783* | (2010.01) | |
| *C07K 14/54* | (2006.01) | |

(52) U.S. Cl.
CPC ............ *A61K 35/17* (2013.01); *C12N 5/0637* (2013.01); *C12N 5/0646* (2013.01)

(58) Field of Classification Search
None
See application file for complete search history.

(56) References Cited

U.S. PATENT DOCUMENTS
2013/0225427 A1  8/2013  Albani

FOREIGN PATENT DOCUMENTS
| | | |
|---|---|---|
| CN | 1489471 A | 4/2004 |
| CN | 102216448 A | 10/2011 |
| EP | 2073009 A1 | 6/2009 |
| WO | WO 2004/078928 A2 * | 9/2004 |
| WO | WO2009/043931 A1 | 4/2009 |
| WO | WO2009/076696 A1 | 6/2009 |

OTHER PUBLICATIONS

Pernick, N (Pathology Outlines, CD19, 2015, pp. 1-3) (Year: 2015).*
Pernick, N (Pathology Outlines, CD16 2015, pp. 1-2) (Year: 2015).*
Pernick, N (Pathology Outlines, CD14, 2015, pp. 1-4) (Year: 2015).*
Pernick, N (Pathology Outlines, CD25, 2015, pp. 1-3) (Year: 2015).*
R&D Systems (2018, rndsystems.com, pp. 1-3) (Year: 2018).*
Engelmann et al (Int. Immunol. 2011, 23(8): 473-484) (Year: 2011).*
Vomhof-DeKrey et al (PNAS, 2015, 112(40): 12474-12479) (Year: 2015).*
Miltenyi Biotec 2019 (Year: 2019).*
Moreira-Teixeira et al (J. Immunol., 2012, 188: 624-631) (Year: 2012).*
Schmidt-Wolf et al (Brit. J. Haematol. 1994, 87: 453-458) (Year: 1994).*
(Trends in Immunol. 2003, 24(7): 364-369) (Year: 2003).*
Wekerle et al (Nature Med. 2012, 18(1): 66-70) (Year: 2012).*
Pilli et al (Front. Immunol. 2017, 8, article 652, pp. 1-17) (Year: 2017).*
Pernick, N (Pathology Outlines.com, 2019) (Year: 2019).*
Zhao et al (Front. Immunol. 2017, 8, article 1578, pp. 1-14) (Year: 2017).*
Liu et al (Clin. Exp. Immunol. 2019, 198: 403-415) (Year: 2019).*
J.J. Subleski et al., "The split personality of NKT cells in malignancy, autoimmune and allergic disorder," Immunotherapy, Oct. 2011, 3(10), pp. 1167-1184.
Moreira-Teixerira et al., "Rapamycin Combined with TGF-b Converts Human Invariant NKT Cells into Suppressive Foxp3+ Regulatory Cells," The Journal of Immunology, vol. 188, Dec. 2011; 9 pages.
Chang et al., "Identification of Bcl-6-dependent follicular helper NKT cells that provide cognate help for B cell responses," Nature Immunology, vol. 13. No. 1, Nov. 27, 2011, 11 pages.
Monteiro et al., "Identification of Regulatory Foxp3+ Invariant NKT Cells Induced by TGF-β," Journal of Immunology, 2010, pp. 2157-2163.
CD Marker Handbook, "Human Mouse," BD Biosciences, www.bdbiosciences.com/go/humancdmarkers, 47 pages.

* cited by examiner

*Primary Examiner* — G. R. Ewoldt
*Assistant Examiner* — Marianne DiBrino
(74) *Attorney, Agent, or Firm* — Muncy, Geissler, Olds & Lowe, P.C.

(57) ABSTRACT

The present invention provides modified natural killer T (NKT) cells, pharmaceutical compositions comprising the modified NKT cells and at least one pharmaceutically acceptable carrier or excipient, and uses of the modified NKT cells. Also disclosed herein are methods for enriching NKT cells and generating the modified natural killer T cells.

14 Claims, 17 Drawing Sheets

Fig. 2E
Fig. 2F
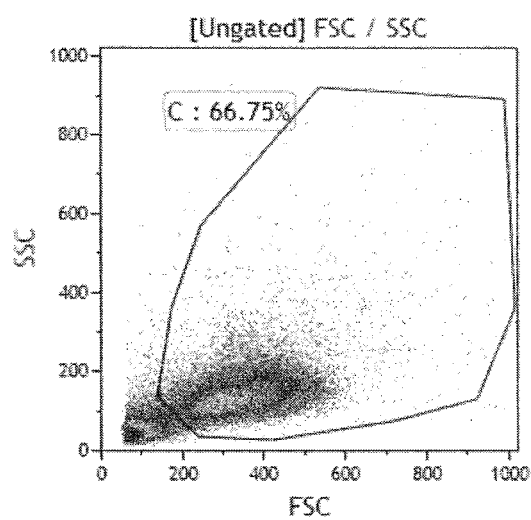
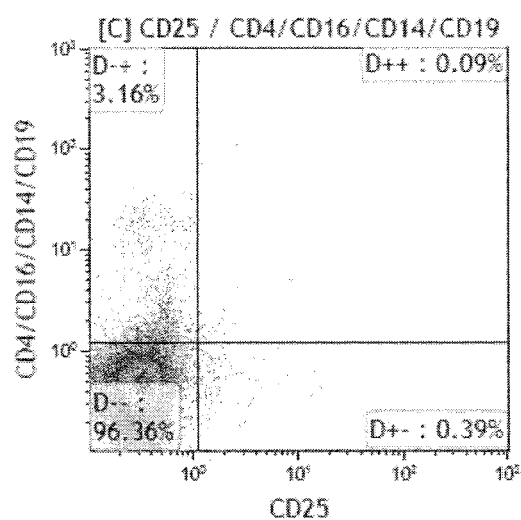

Fig 6A
Fig 6B
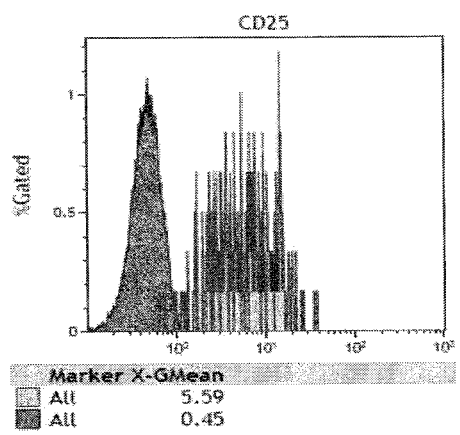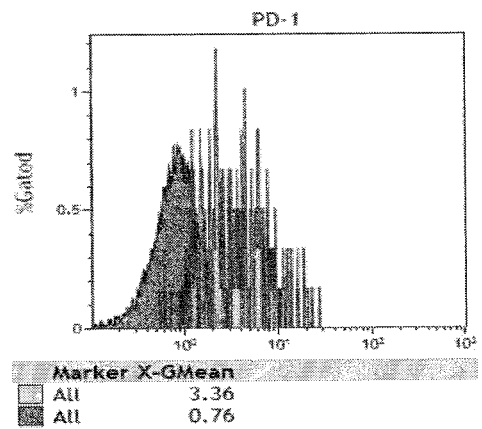
Fig. 6C
Fig. 6D
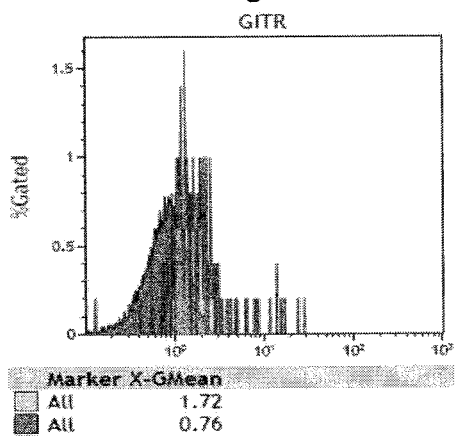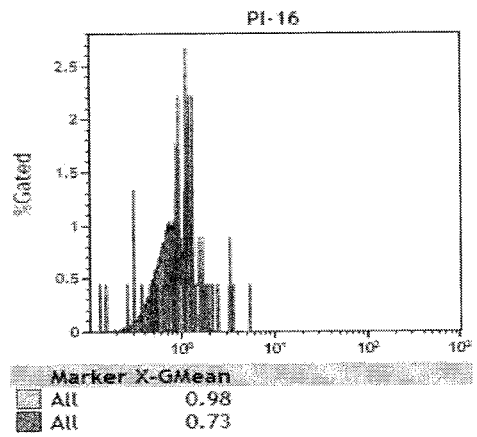
Fig. 6E
Fig. 6F
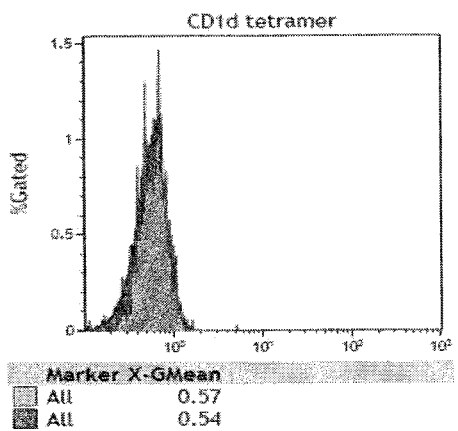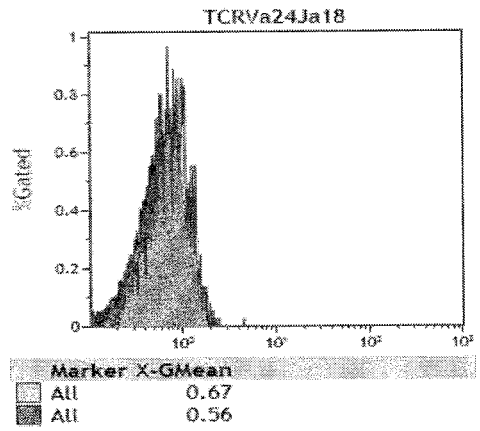

MODIFIED NATURAL KILLER T CELLS, PHARMACEUTICAL COMPOSITIONS AND USES THEREOF

CROSS-REFERENCE TO RELATED APPLICATIONS

This application claims the benefit of U.S. Application No. 62/144,066, filed on 7 Apr. 2015, the entire disclosure of which is incorporated herein by reference.

BACKGROUND

Natural Killer T (NKT) cells and conventional T cells develop in the thymus from a common precursor. However, distinct intrathymic T cell receptor (TCR) interactions activate cell-specific transcriptional programs that instruct the unique functions of each cell type. NKT cells are selected by TCR interactions with CD4/CD8 double positive thymocytes expressing endogenous glycolipids in the context of CD1d molecules. By contrast, conventional T cells are selected by TCR interactions with thymic epithelial cells expressing peptides in the context of MHC molecules (Jeff Subleski et al. The split personality of NKT cells in malignancy, autoimmune and allergic disorders. Immunotherapy. 2011 Oct.; 3(10): 1167-1184).

The breakdown of mechanisms assuring the recognition of self and non-self is a hallmark feature of autoimmune diseases. The protracted immune response(s) targeting self-tissues lead to prolonged inflammation and subsequent tissue destruction. The aberrant frequency and/or function of NKT cells in the peripheral blood of patients with autoimmune diseases suggest the involvement of NKT cells in disease pathology.

These findings raise the possibility of developing a NKT cell-based therapy for autoimmune disease and culture methods to generate greater number of therapeutically competent NKT cells for clinical applications, as there is still an unmet need for effective treatment and/or prevention for autoimmune diseases.

The present invention provides modified NKT cells having a unique phenotype to satisfy these and other needs. The modified NKT cells can be used in autologous therapy or in non-autologous therapy.

SUMMARY OF THE INVENTION

In one embodiment, the present invention provides a modified NKT cell comprising a $CD3^+CD56^+CD8^+$ NKT cell phenotype; at least one regulatory T (Treg) cell surface markers selected from CD25, Foxp3, CTLA-4 or LAP; and a T helper cell surface marker selected from PD-1.

In another embodiment, the present invention provides a modified NKT cell comprising a $CD3^+CD56^+CD8^+$ NKT cell phenotype; at least one Treg cell surface markers selected from CD25, Foxp3, CTLA-4 or LAP; a T helper cell surface marker selected from PD-1, wherein the NKT phenotype is substantially free of at least one invariant natural killer T (iNKT) cell surface marker selected from CD1d-tetramer or TCR Vα24_Jα18, wherein the NKT phenotype is substantially free of at least one cell marker selected from GITR, PI-16 or IL-15Rα.

In another embodiment, the present invention provides a modified NKT cell comprising a $CD3^+CD56^+CD8^+$ NKT cell phenotype; at least one Treg cell surface markers selected from CD25, Foxp3, CTLA-4 or LAP; a T helper cell surface marker selected from PD-1, a T cell growth receptor selected from IL-15Rα, wherein the NKT phenotype is substantially free of at least one iNKT cell surface marker selected from CD1d-tetramer or TCR Vα24_Jα18, wherein the NKT phenotype is substantially free at least one a cell marker selected from GITR or PI-16.

In other embodiments, the present invention provides pharmaceutical compositions comprising one or more modified NKT cells described herein and a pharmaceutically acceptable carrier or excipient.

Some embodiments provide methods for treating an autoimmune disease, comprising administering an effective amount of the modified NKT cells or the pharmaceutical composition described herein to a subject in need thereof to thereby treat the autoimmune disease.

The present invention also provides methods for generating the modified NKT cell described herein, comprising (a) culturing an enriched mononuclear cell fraction, wherein the mononuclear cells in the enriched cell fraction are substantially free of at least one of the following cell markers: CD14, CD19, or CD25 (hereafter enriched $CD14^-CD19^-CD25^-$ cell fraction), with transforming growth factor beta (TGF-β) and a cell culture medium, and (b) contacting the cultured $CD14^-CD19^-CD25^-$ cell fraction from step (a) with a T-cell growth factor.

In another embodiment, methods for generating the modified NKT cell of the present invention comprises the steps of (a) culturing an enriched mononuclear cell fraction, wherein the mononuclear cells in the enriched cell fraction are substantially free of at least one of the following surface markers: CD4, CD14, CD16, CD19, or CD25 (hereafter enriched $CD4^-CD14^-CD16^-CD19^-CD25^-$ cell fraction), with transforming growth factor beta (TGF-β) and a cell culture medium, and (b) contacting the cultured $CD4^-CD14^-CD16^-CD19^-CD25^-$ cell fraction from step (a) with a T-cell growth factor.

The enrichment and/or culture methods described herein generate a greater number of modified NKT cells from a fixed amount of a sample (for example, 10 ml of heparinized peripheral blood) with a higher immunosuppressive activity.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

BRIEF DESCRIPTION OF THE DRAWINGS

Illustrative embodiments of the present invention are described in detail below with reference to the following Figures:

FIG. 2A-2F are fluorescence-activated cell sorting (FACS) images illustrating the expression of CD4, CD14, CD16, CD19 and CD25 cell surface markers on natural NKT cells (FIG. 2A-2B), the enriched CD14$^-$CD19$^-$CD25$^-$ cell fraction (FIG. 2C and FIG. 2D) and the enriched CD4$^-$CD14$^-$CD16$^-$CD19$^-$CD25$^-$ cell fraction (FIG. 2E and FIG. 2F).

FIG. 6A-6L are histograms illustrating the expression of CD25 (FIG. 6A), PD-1 (FIG. 6B), GITR (FIG. 6C), PI-16 (FIG. 6D), CD tetramer (FIG. 6E), TCR Vα24_Jα18 (FIG. 6F), CTLA-4 (FIG. 6G), LAP (FIG. 6H), IL-15Rα (FIG. 6I), Foxp3 (FIG. 6J) CD4, CD14, CD16 and CD19 (FIG. 6K) and CD3 (FIG. 6L) of the modified NKT cells in Example 3.

FIG. 7A shows the in vitro proliferation of T lymphocytes without any stimulation, FIG. 7B shows the in vitro proliferation of T lymphocytes responder cells with anti-CD3 and anti-CD28 antibody stimulation and FIG. 7C shows the suppressive effect of the modified NKT cells on T lymphocyte responder cell proliferation with anti-CD3 and anti-CD28 antibody stimulation.

FIG. 8A shows the in vitro proliferation of T lymphocytes without any stimulation, FIG. 8B shows the in vitro proliferation of T lymphocytes responder cells with anti-CD3 and anti-CD28 antibody stimulation and FIG. 8C shows the suppressive effect of the modified NKT cells on T lymphocyte responder cell proliferation with anti-CD3 and anti-CD28 antibody stimulation.

DETAILED DESCRIPTION OF THE INVENTION

Figure 1A:
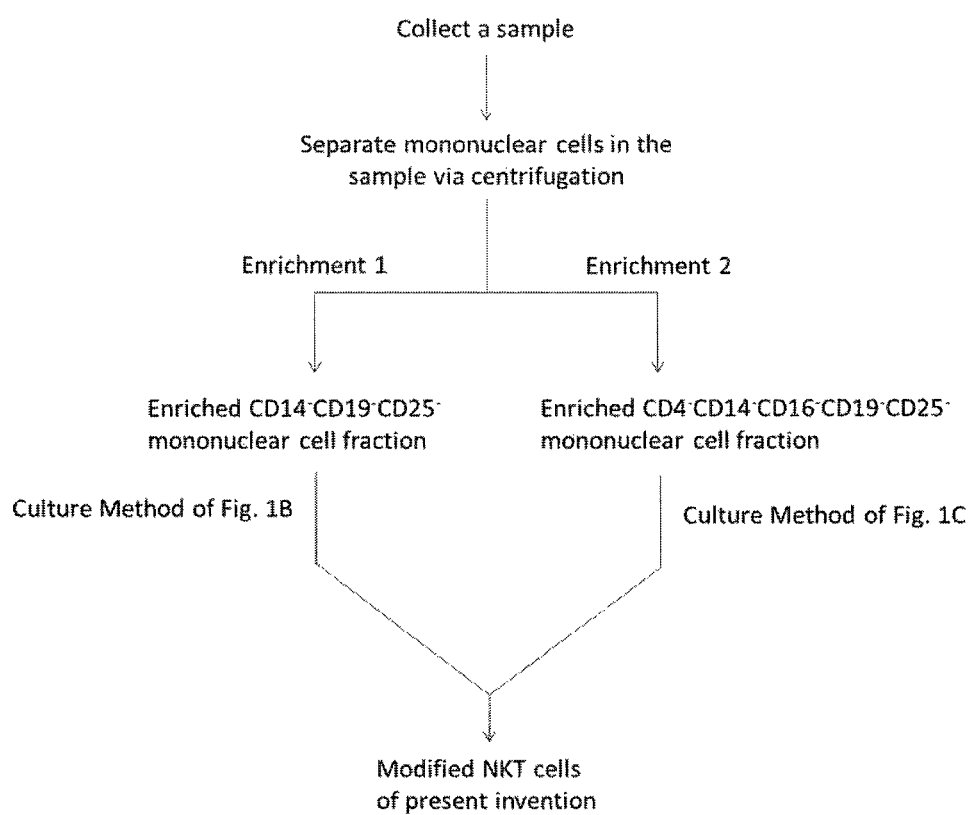
FIG. 1A illustrates schematically two embodiments of mononuclear cell enrichment and FIG. 1B and FIG. 1C illustrate schematically the two embodiments of culture method for generating the modified NKT cells of the present invention.

As used herein, the articles "a" and "an" refer to one or more than one (i.e., at least one) of the grammatical object of the article. By way of example, "a modified NKT cell" means one modified NKT cell or more than one modified NKT cells.

An "effective amount," as used herein, refers to a dose of the modified NKT cells or pharmaceutical composition that is sufficient to reduce IL-10 level or the symptoms and signs of autoimmune disease, which include, but are not limited to, weight loss, skin rash, abdominal pain, itchy eyes, joint pain or swelling.

The term "subject" can refer to a vertebrate having autoimmune disease or to a vertebrate deemed to be in need of autoimmune disease treatment or in need of increasing IL-10 level. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

The expression level or surface density of a cell surface marker, such as CD25, Foxp3, PD-1, on the surface of NKT cells is "+" as long as the expression is positive relative to a negative control population, expressed as "−". In one exemplary embodiment, "+" means that the cellular surface marker is detectably present in fluorescence activated cell sorting or magnetic beads over an isotype control; or is detectable above background in quantitative or semi-quantitative RT-PCR. In another exemplary embodiment, "−" means that the cellular marker is not detectably present in fluorescence activated cell sorting or magnetic beads over an isotype control; or is not detectable above background in quantitative or semi-quantitative RT-PCR. In one example, "+" expression of a surface marker means the net mean fluorescent intensity (MFI) of the surface marker is greater than or equal to about 0, about 1, about 1.5, about 2, about 2.5, about 3, about 3.5, about 4, about 4.5, or about 5. In another example, "−" expression of a surface marker means the net MFI of the surface marker is less than or equal to about 5, about 4.5, about 4, about 3.5, about 3, about 2.5, about 2, about 1.5, about 1, about 0.5, about 0.

The terms "T cell" and "T lymphocyte" are used interchangeably throughout this patent.

The term "substantially free" as used herein includes "−" expression of a cell marker or the level of a cell marker is undetectable or minimally detected by routine analytical methods used in the field. For example, FACS/flow cytometry, as well as other analytical methods known to the skilled artisan.

All numbers herein may be understood as modified by "about." In one embodiment, the term "about," when referring to a measurable value such as an amount, a temporal duration, and the like, is meant to encompass variations of ±10%, preferably ±5%, more preferably ±1%, and even more preferably ±0.1% from the specified value, as such variations are appropriate to the dosage of the therapeutic agent, unless other specified. As used herein, the term "about," when referring to a range, is meant to encompass variations of ±10% within the difference of the range, preferably ±5%, more preferably ±1%, and even more preferably ±0.1% from the specified value, as such variations are appropriate to the dosage of the therapeutic agent, unless other specified.

Modified NKT Cell

Naturally occurring or conventional NKT cells have CD3$^+$CD56$^+$CD8$^+$ phenotype. In an exemplary embodiment, the naturally occurring or conventional NKT cells have a CD14$^-$CD19$^-$CD3$^+$CD56$^+$CD8$^+$CD4$^-$CD25$^-$Foxp3$^-$ PD-1$^-$CTLA-4$^-$GITR$^-$ PI-16$^-$CD1d tetramer$^-$LAP$^-$ TCR Vα24_Jα18$^-$ phenotype.

In one embodiment, the present invention provides a modified NKT cell comprising a CD3+CD56+CD8+ NKT cell phenotype; at least one regulatory T (Tregs) cell surface markers selected from CD25, Foxp3, CTLA-4, or LAP; and a T helper cell surface marker, such as PD-1, as illustrated in Table 1, FIG. 5A-FIG. 5M and FIG. 6A-FIG. 6L. Without being bound by any particular theory, it is believed that the modified NKT of the present invention have immunosuppressive properties similar to those of Treg cells, and/or T helper cell, such as the production of IFN-γ. In another embodiment, the present invention provides a modified NKT cell comprising a CD3+CD56+CD8+ NKT cell, wherein said CD3+CD56+CD8+ NKT cell further comprises at least one Treg cell surface markers selected from CD25, Foxp3, PD-1, CTLA-4, or LAP, and a T helper cell surface marker, such as PD-1, as illustrated in Table 1.

In an exemplary embodiment, the modified NKT cell comprises CD14−CD19− CD3+CD4−CD16−CD56+CD8+ CD25+Foxp3+PD-1+CTLA-4+GITR−PI-16−CD1d tetramer− LAP+ TCR Vα24_Jα18−IL-15Rα+ phenotype. In another exemplary embodiment, the modified NKT cell comprises CD14−CD19−CD3+CD4−CD16−CD56+CD8+ CD25+Foxp3+PD-1+CTLA-4+GITR−PI-16−CD1d tetramer−LAP+TCR Vα24_Jα18−IL-15Rα− phenotype.

TABLE 1

Phenotypes of conventional NKT cells and modified NKT cells

| Cell Surface marker | Enriched CD14−CD19−CD25− cell fraction or enriched CD4−CD14−CD16−CD19−CD25− cell fraction | Modified NKT Cell (cultured from enriched CD14−CD19−CD25− cell fraction) | Modified NKT Cell (cultured from enriched CD4−CD14−CD16−CD19−CD25− cell fraction) |
|---|---|---|---|
| CD14 | − | − | − |
| CD19 | − | − | − |
| CD3 | + | + | + |
| CD4 | − | − | − |
| CD16 | − | Not tested | − |
| CD56 | + | + | + |
| CD8 | + | + | + |
| CD25 | − | + | + |
| Foxp3 [a] | − | + | + |
| PD-1 [b] | − | + | + |
| CTLA-4 [c] | − | + | + |
| GITR [d] | − | − | − |
| PI-16 [e] | − | − | − |
| CD1d tetramer | − | − | − |
| LAP [f] | − | + | + |
| TCR Vα24_Jα18 [g] | − | − | − |
| IL-15Rα [h] | − | + | − |

[a] Forkhead box P3
[b] Programmed death-1
[c] Cytotoxic T lymphocyte-associated molecule-4
[d] glucocorticoid-induced tumor necrosis factor receptor
[e] peptide inhibitor 16
[f] latency-associated peptide
[g] T cell receptor V alpha 24 J alpha 18
[h] Interleukin-15 receptor α

In one embodiment, the present invention provides modified NKT cells generated from enriched CD4−CD14−CD16−CD19−CD25− mononuclear cell fraction and comprise a CD3+CD56+CD8+ NKT cell phenotype; at least one Treg cell surface markers selected from CD25, Foxp3, CTLA-4 or LAP; and a T helper cell surface marker selected from PD-1, wherein the NKT phenotype is substantially free of at least one iNKT cell surface marker selected from CD1d-tetramer or TCR Vα24_Jα18, wherein the NKT phenotype is substantially free of at least one cell surface marker selected from GITR, PI-16 or IL-15Rα. In another embodiment, the modified NKT cells are generated from enriched CD14CD19−CD25− mononuclear cell fraction and comprise a CD3+CD56+CD8+ NKT cell phenotype; at least one Treg cell surface markers selected from CD25, Foxp3, PD-1, CTLA-4 or LAP; a T helper cell surface marker selected from PD-1; and a T cell growth receptor selected from IL-15Rα, wherein the NKT phenotype is substantially free of at least one iNKT cell surface marker selected from CD1d-tetramer or TCR Vα24_Jα18, wherein the NKT phenotype is substantially free of at least one cell surface receptor selected from GITR or PI-16.

In one embodiment, the net MFIs of the following cell markers are greater than or equal to about 0, about 0.5, about 1, about 1.5, about 2, about 2.5, about 3, about 3.5, about 4, about 4.5 or about 5: CD3, CD56, CD8, CD25, Foxp3, PD-1, CTLA-4, LAP or IL-15Rα. In another embodiment, the net MFIs of the following cell markers are less than or equal to about 5, about 4.5, about 4, about 3.5, about 3, about 2.5, about 2, about 1.5, about 1, about 0.5, about 0: CD14, CD19, CD4, CD16, GITR, PI-16, CD1d tetramer, TCR Vα24_Jα18 or IL-15Rα.

In some embodiments, the modified NKT cells of the present invention are substantially free of at least one of the following cell surface markers: CD14, CD19, CD4, CD16, GITR, PI-16, CD1 d tetramer, TCR Vα24_Jα18, or IL-15 Rα. In one exemplary embodiment, the modified NKT cells comprise a CD3+CD56+CD8+ NKT cells phenotype, wherein said CD3+CD56+CD8+ NKT cells are substantially free of at least one iNKT cell surface marker selected from CD1 d-tetramer (e.g., CD1d-tetramer), or TCR Vα24_Jα18 (e.g., TCR Vα24_Jα18−). In another exemplary embodiment, the modified NKT cells comprise CD3+CD56+CD8+ NKT cells phenotype, wherein said CD3+CD56+CD8+ NKT cells are substantially free of GITR (e.g., GITR). In yet another exemplary embodiment, the modified NKT cells are substantially free of PI-16 cell surface marker (e.g., PI-16−). In yet another exemplary embodiment, the modified NKT cells are substantially free of a T cell growth receptor, such as IL-15Rα (e.g., IL-15Rα−).

In one embodiment, the expression level or surface density of the cell surface marker is quantified by exposing the modified NKT cells to one or more fluorescent dye-tagged specific anti-human monoclonal antibodies listed in Table 2, followed by sorting of the modified NKT cells using flow cytometry (e.g. Gallios, commercially available from Beckman Coulter, Inc., USA). Other methods for quantifying the expression level of the cell marker are known, or will be apparent, to those skilled in the art.

The modified NKT cells can be from a single individual, i.e., autologous, or pooled from multiple individuals (non-autologous allogeneic).

Pharmaceutical Composition

The present invention provides pharmaceutical compositions comprising a modified NKT cell described herein, and a pharmaceutically acceptable carrier or excipient.

Routes of administering the present pharmaceutical compositions or modified NKT cells include, but are not limited to, intravenous, intramuscular, intraarticular, subcutaneous, oral, topical, subcutaneous, intradermal, transdermal, subdermal, parenteral, rectal, spinal, or epidermal administration. In one embodiment, the modified NKT cells or the pharmaceutical compositions are administered by intravenous injection or infusion.

The pharmaceutical compositions of the present invention can be prepared as injectables, either as liquid solutions or suspensions, or as solid forms which are suitable for solution or suspension in liquid vehicles prior to injection. The pharmaceutical composition can also be prepared in solid form, emulsified or other particulate carriers used for sustained delivery. For example, the pharmaceutical composition can be in the form of an oil emulsion, water-in-oil emulsion, water-in-oil-in-water emulsion, site-specific emulsion, long-residence emulsion, sticky emulsion, micro emulsion, nano emulsion, liposome, microparticle, microsphere, nanosphere, nanoparticle and various natural or synthetic polymers, such as nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the pharmaceutical composition.

The present modified NKT cells are formulated into pharmaceutical compositions for delivery to a mammalian subject. The pharmaceutical composition is administered alone, and/or mixed with a pharmaceutically acceptable vehicle, excipient or carrier. Suitable vehicles are, for example, saline, dextrose, glycerol, or the like, and combinations thereof. In addition, the vehicle can contain minor amounts of auxiliary substances such as wetting or emulsifying agents, pH buffering agents, or adjuvants. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextran, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives. See e.g., the 21st edition of Remington's Pharmaceutical Science, Mack Publishing Company, Easton, Pa. ("Remington's"). The pharmaceutical compositions of the present invention can also include ancillary substances, such as pharmacological agents, cytokines, or other biological response modifiers.

Actual methods of preparing such dosage forms are known, or will be apparent, to those skilled in the art. See, e.g., Remington's Pharmaceutical Sciences, Mack Publishing Company, Easton, Pa., 21st edition.

The modified NKT cells or the present pharmaceutical compositions can be administered in a single dose treatment or in multiple dose treatments on a schedule and over a time period appropriate to the age, weight and condition of the subject, the particular composition used, and the route of administration, whether the modified NKT cells or the present pharmaceutical composition is used for prophylactic or curative purposes, etc. For example, in one embodiment, the modified NKT cells or pharmaceutical composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of the modified NKT cells or the pharmaceutical composition according to the invention, e.g., the period of time over which the modified NKT cell or pharmaceutical composition is administered, can vary, depending on any of a variety of factors, e.g., subject response, etc. For example, the modified NKT cells or pharmaceutical composition can be administered over a period of time ranging from about one or more seconds to one or more minutes, one or more hours to one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

It is advantageous to formulate parenteral pharmaceutical compositions or modified NKT cells in dosage unit form for ease of administration and uniformity of dosage. Dosage unit form as used herein refers to physically discrete units suited as unitary dosages for the subject to be treated; each unit containing a predetermined quantity of modified NKT cells calculated to produce the desired therapeutic effect in association with the required pharmaceutical carrier.

The data obtained from the cell culture assays and animal studies can be used in formulating a range of dosage for use in humans. In one embodiment, the dosage of such NKT cells lies within a range of circulating concentrations that include the $ED_{50}$ with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the $IC_{50}$ (i.e., the concentration of the modified NKT cells which achieves a half-maximal inhibition of symptoms) as determined in cell culture. Sonderstrup, Springer, Sem. Immunopathol. 25: 35-45, 2003. Nikula et al., Inhal. Toxicol. 4(12): 123-53, 2000.

The pharmaceutical composition is formulated to contain an effective amount of the modified NKT cells, wherein the amount depends on the subject to be treated and the condition to be treated. The specific dose level for any particular subject depends upon a variety of factors including the activity of the specific modified NKT cells, the age, body weight, general health, sex, diet, time of administration, route of administration, and rate of excretion, drug combination and the severity of the particular disease undergoing therapy. An exemplary, non-limiting range for a therapeutically or prophylactically effective amount of the modified NKT cells of the present invention is at least about 10 cells per dose to about $1\times10^{10}$ per dose. Other dosages are also possible, including, but not limited to, $1\times10^2$, $1\times10^3$, $1\times10^4$, $1\times10^5$, $1\times10^6$, $1\times10^7$, $1\times10^8$ or $1\times10^9$.

Methods for Treating an Autoimmune Disease

The modified NKT cells of the present invention have immunosuppressive properties similar to those of Treg cells. In one embodiment, the invention provides methods for treating autoimmune disease by administering to a subject in need thereof the modified NKT cells or the pharmaceutical composition described herein in an amount effective to treat autoimmune disease. Without being bound by any particular theory, it is believed that the modified NKT cells exert a therapeutic effect on the autoimmune disease by increasing T helper 1 response (IFN-γ secretion) or exerting immunosuppressive properties. In one embodiment, the immunosuppressive property is the suppression of autoreactive and activated T lymphocytes, which is a key player in autoimmune diseases.

As used herein, an "autoimmune disease" is a disease or disorder arising from and directed against an individual's own tissues. Autoimmune diseases include, but are not limited to, Type I diabetes, multiple sclerosis, Hashimoto's Thyroiditis, Grave's disease, psoriasis, systemic lupus erythematosus (SLE), Sjoren's Syndrome, celiac disease, lichen planus and rheumatoid arthritis, lupus allergic dermatitis, scleroderma, atopic eczema, sinusitis, asthma, inflammatory bowel disease such as ulcerative colitis.

The modified NKT cells may be administered alone, or before, after or simultaneously with one or more immunosuppressive agents. Non limiting examples of immunosuppressive agent include steroid, a nonsteroidal anti-inflammatory drug (NSAID) such as indomethacin, a disease-modifying anti-rheumatic drug (DMARD) or a combination of two or more of the foregoing. DMARDs include small molecule agents, such as methotrexate, leflunomide, sulfasalazine, cyclophosphamide, azathioprine, cyclosporin A, d-penicillamine, antimalarial drugs (e.g. hydroxychloroquine). DMARDs also include biological substances, such as a Tumor necrosis factor α (TNF-α) antagonist (e.g. Etanercept, trade name Enbrel, commercially available from Wyeth Pharmaceuticals, Inc., Collegeville, USA, Adalimumab, trade name HUMIRA, commercially available from Abbott Laboratories, Abbott Park, Ill., USA), interleukin-1 receptor antagonist, interleukin-6 receptor antagonist, anti-CD20 monoclonal antibody, CTLA-4-Ig, RGD peptide and the like.

Methods of Enriching NKT Cells and Uses Thereof to Generate Modified NKT Cells

As illustrated in FIG. 1A, a sample (e.g., peripheral blood, cord blood, bone marrow, tissue sample from the thymus or the spleen) is obtained from a subject and mononuclear cells in the sample are isolated by centrifugation (e.g., Ficoll-Paque™ PREMIUM, GE Healthcare USA). Other methods of isolating or separating mononuclear cells are known, or will be apparent, to those skilled in the art. The isolated mononuclear cells can be further enriched to obtain only T cells.

In one embodiment, the mononuclear cells with at least of the following surface markers: CD4, CD14, CD16, CD19 or CD25 are depleted from the isolated mononuclear cell fraction. Depending on the source of the sample, the mononuclear cell can be derived from human peripheral mononuclear cell, monocyte or myeloid progenitor cell. In one embodiment, the mononuclear cells in the enriched $CD14^-CD19^-CD25^-$ cell fraction are substantially free of the cell surface markers selected from CD14, CD19 or CD25. In another embodiment, the mononuclear cells in the enriched $CD4^-CD14^-CD16^-CD19^-CD25^-$ cell fraction are substantially free of the cell surface markers selected from CD4, CD14, CD16, CD19 or CD25.

Figure 1B:
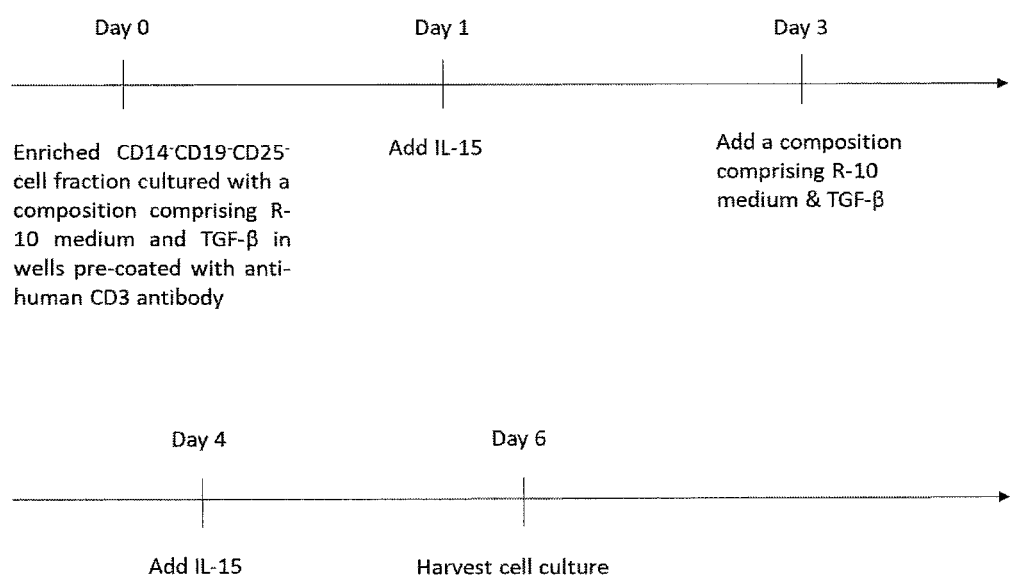

In one embodiment, as illustrated in FIG. 1A and FIG. 1B, the in vitro method to generate modified NKT cells comprises the following phases: (i) deplete mononuclear cells with at least one of the following cell markers: CD14, CD19 or CD25 (i.e., resulting in an enriched $CD14^-CD19^-CD25^-$ mononuclear cell fraction); (ii) contacting the $CD14^-CD19^-CD25^-$ cell fraction from step (i) with a composition comprising transforming growth factor beta (TGF-β) and a cell medium; and (iii) contacting the enriched $CD14^- CD19^- CD25^-$ NKT cell fraction from step (ii) with a T-cell growth factor. In another embodiment, the in vitro method to generate modified NKT cells comprises the following phases: (i) deplete mononuclear cells with at least one of the following cell markers: CD4, CD14, CD16, CD19 or CD25 (i.e., resulting in an enriched $CD4^-CD14^-CD16^-CD19^-CD25^-$ mononuclear cell fraction); (ii) contact the enriched $CD4^-CD14^-CD16^-CD19^- CD25^-$ cell fraction from step (i) with a composition comprising TGF-β and a cell culture medium; (iii) contacting the mononuclear cell fraction from step (ii) with a T-cell growth factor.

In one embodiment, contacting the enriched NKT cells with TGF-β, T-cell growth factor and a cell culture medium enhances the expression of Treg cell surface markers such as CD25, Foxp3 and CTLA-4 on the modified NKT cells. In another embodiment, the culturing method enhances the expression of T helper cell surface markers such PD-1. Proliferation rate of the modified NKT cells was determined by FACS, based on the signal intensity of modified $CD3^+CD56^+CD8^+$ NKT cells. Other assays for cell proliferation are well known in the art, e.g., clonogenic assays, metabolic assays, and direct proliferation assays.

Cell culture medium, as used herein, includes any medium that support the growth and/or maintenance of cells. Non limiting examples of cell culture medium include hematopoietic cell medium, such as X-Vivo 15 or a mixture comprising a mammalian cell medium and a media supplements, such as R-10 medium.

The term mammalian cell medium include any cell medium that support the growth and/or maintenance of mammalian cells, such as the RPMI medium 1640 (commercially available from Thermo Fisher Scientific, USA). In one embodiment, the RPMI medium 1640 comprises 100 U/mL penicillin; 100 µg/mL streptavidin; 2 mM L-glutamine; and 20 mM HEPES. Media supplement provide nutrients such as lipid, amino acids, growth factors, glucose or trace elements to mammalian cell culture to increase yield. Non-limiting examples of media supplement are blood serum, such as about 5% to about 10% fetal bovine serum (FBS). In one embodiment, R-10 medium comprises RPMI medium 1640 and 10% of FBS.

T cell growth factor includes any molecules that stimulate the production and development of T cells. Non limiting example of T-cell growth factor includes IL-15. In one embodiment, the concentration of IL-15 is about 20 ng/ml to about 160 ng/ml. In another embodiment, the concentration of IL-15 is equal to or less than about 160, 150, 140, 130, 120, 110, 100, 90, 80, 70, 60, 50, 40, 30 or 20 or any value or range of values therebetween in 1 ng/ml increments (e.g. about 155 ng/ml, about 37 ng/ml).

Although IL-2 can be used to generate modified NKT cells, the number of modified NKT cells generated by IL-2 is less compare to that of IL-15 (see Table 6). IL-2 and IL-15 are cytokines with overlapping but distinct biological effects, their receptors share two subunits that are essential for signal transduction. Without being bound by any particular theory, it is believed that IL-15 has a higher affinity to its private receptor a and hence, a lower concentration of IL-15 is required to generate the modified NKT cells. In one embodiment, the T-cell growth factor is substantially free of IL-2. In another embodiment, IL-2, is present in the T-cell growth factor in an amount of ≤2 weight %, ≤1.5 weight %, ≤1 weight %, and ≤0.5 weight %. An exemplary non-limiting range for the contact time of the enriched NKT cells with transforming growth factor beta (TGF-β) the cell culture medium or the T-cell growth factor and is from about 1 minute to about 1 hour, from about 1 hour to about 24 hours, from about 1 day to about 3 days, from about 1 day to about 6 days, from about 1 day to about 9 days, from about 3 days to about 6 days, or at least 1 day. In one embodiment, the contact time is about 3 days. In another embodiment, the contact time is about 6 days.

The following examples of specific aspects for carrying out the present invention are offered for illustrative purposes only, and are not intended to limit the scope of the present invention in any way.

EXAMPLES

Example 1

Enriched Mononuclear Cell Fractions

As illustrated in FIG. 1A, 40 ml of peripheral blood was collected from a healthy volunteer and heparinized. The blood sample was mixed with equal volume of pre-warmed phosphate-buffered saline (PBS) (Biological Industries, Israel). The 40 ml diluted peripheral blood aliquot was placed into a 50 ml centrifuge tube and downloaded 10 ml pre-warmed Ficoll-Paque™ PREMIUM. The centrifuge tube was centrifuged at 2000 rpm, in room temperature for 30 min. The mononuclear cells were isolated from other types of blood cells, then collected and washed once in PBS. The cell pellet was re-suspended into a density of $10^6/100$ µl MACS buffer.

To deplete or remove mononuclear cells with at least one of the following cell markers: CD4, CD14, CD16, CD19 or CD25, the isolated mononuclear cells from the preceding paragraph were subjected to immunomagnetic bead separation using "QuadroMACS Separator" (Miltenyi Biotec Bergisch, Gladbach, Germany), according to the manufacturer's instructions. Briefly, the mononuclear cells were stained with biotin-anti-CD14 antibody, biotin-anti-CD19 antibody, biotin-anti-CD25 antibody, biotin-anti-CD4 antibody and/or biotin-anti-CD16 antibody (all of them were commercially available from BioLegend) and 20 µl of Streptavidin Microbeads (Miltenyi Biotech, Germany), and separated with a magnetic separator. The $CD14^-CD19^-CD25^-$ mononuclear cell fraction or $CD4^-CD14^-CD16^-$ $CD19^-CD25^-$ mononuclear cell fraction was enriched from unbound cells by washing. The enriched $CD14^-CD19^-$ $CD25^-$ mononuclear cell fraction are substantially free of the cell with at least one cell surface marker selected from CD14, CD19 or CD25, whereas the enriched $CD4^-CD14^-CD16^-$ $CD19^-CD25^-$ mononuclear cell fraction is substantially free of the cells with at least one cell surface marker selected from CD4, CD14, CD16, CD19 or CD25.

Figure 2A:
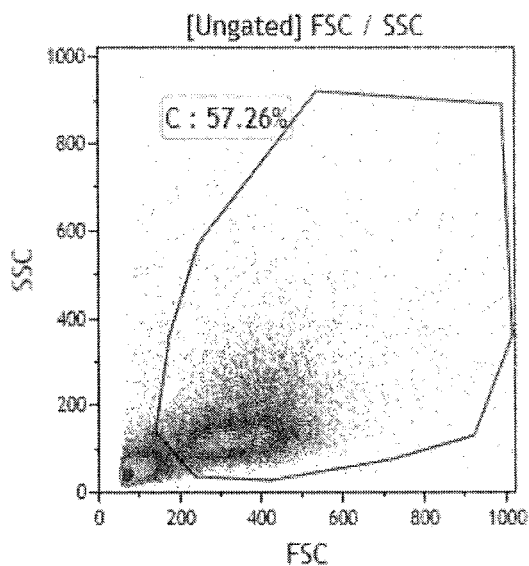
Figure 2B:
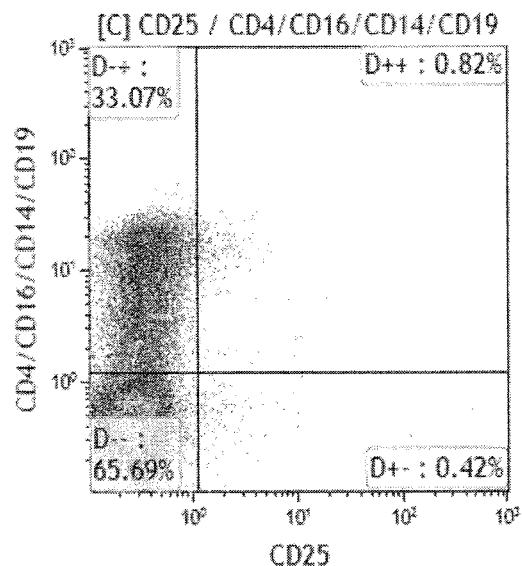
Figure 2C:
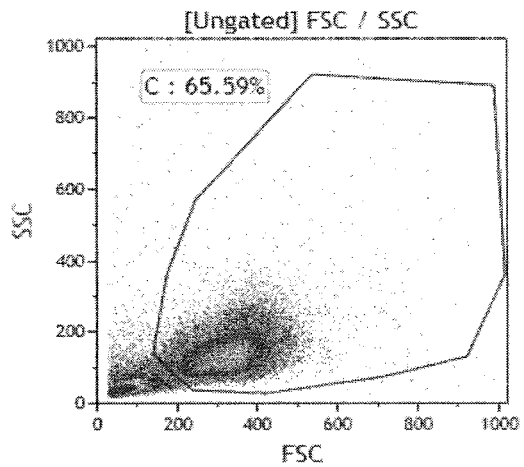
Figure 2D:
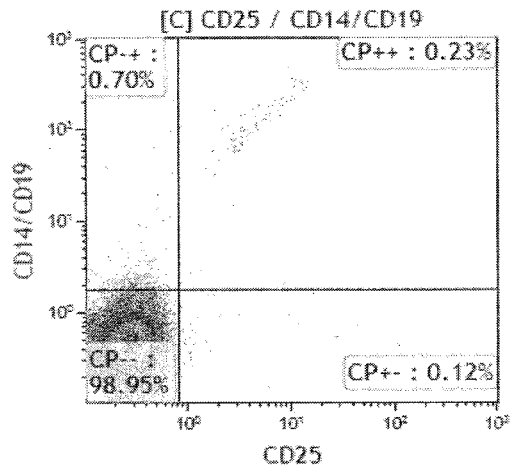
Figure 3A:
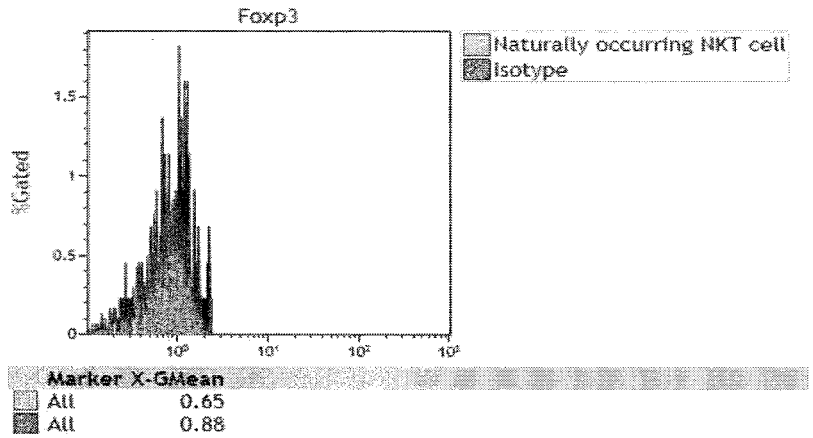
FIG. 3A-3M are histograms illustrating the expression of Foxp3 (FIG. 3A), CD25 (FIG. 3B), PD-1 (FIG. 3C), GITR (FIG. 3D), PI-16 (FIG. 3E), CD1d tetramer (FIG. 3F), TCR Vα24_Jα18 (FIG. 3G), CTLA-4 (FIG. 3H), LAP (FIG. 3I), IL-15Rα (FIG. 3J), CD14 and CD19 (FIG. 3K), CD4 (FIG. 3L) and CD3 (FIG. 3M) of the enriched CD14$^-$ CD19$^-$ CD25 cell fraction.
Figure 3B:
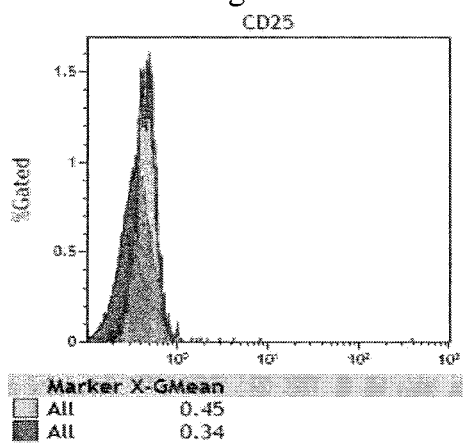
Figure 3C:
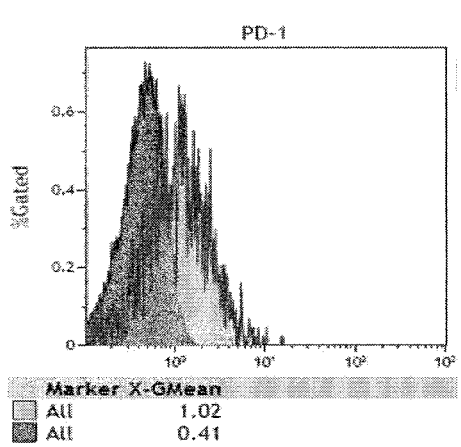
Figure 3D:
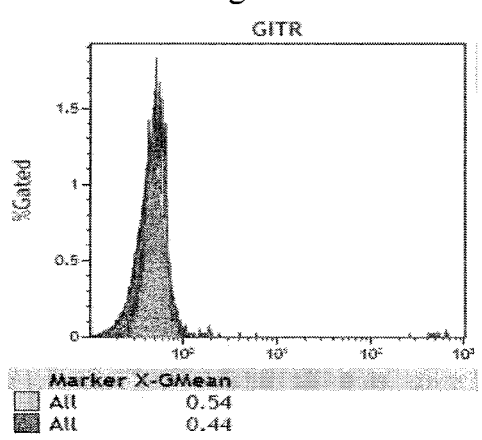
Figure 3E:
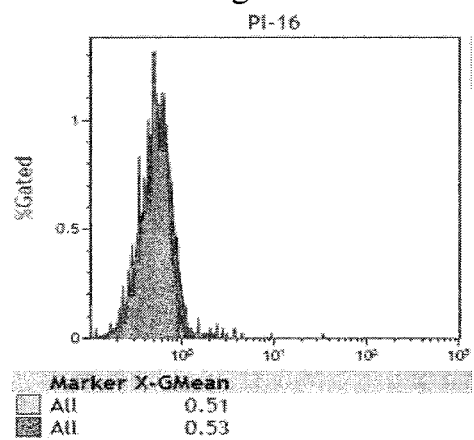
Figure 3F:
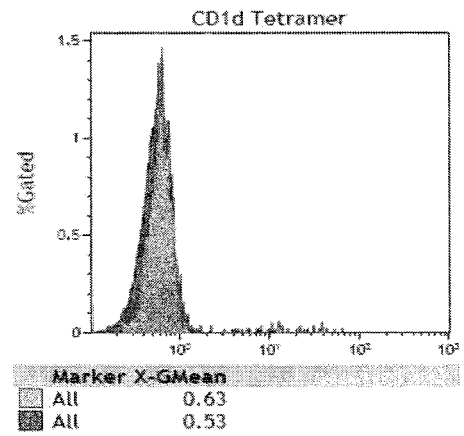
Figure 3G:
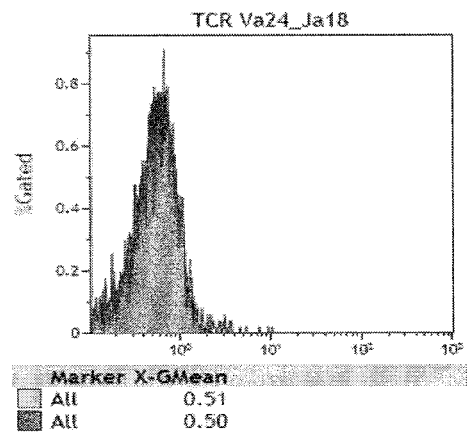
Figure 3H:
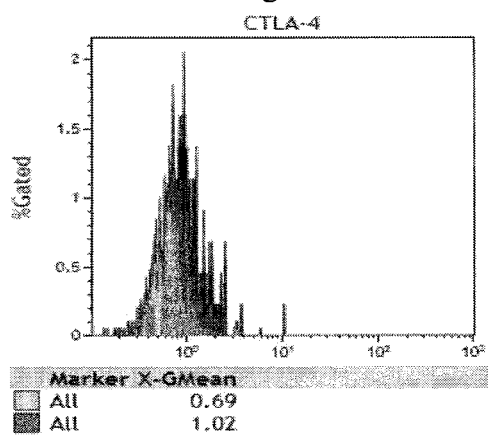
Figure 3I:
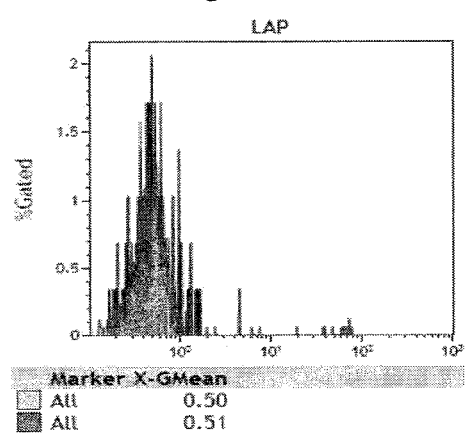
Figure 3J:
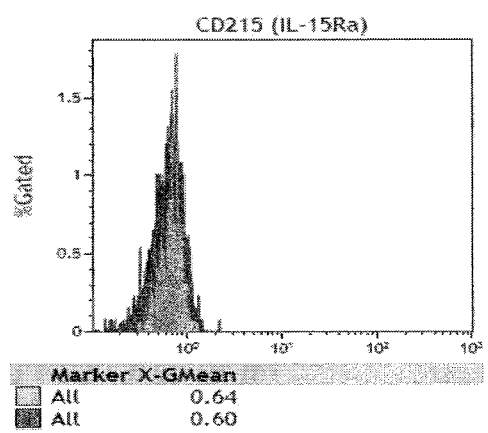
Figure 3K:
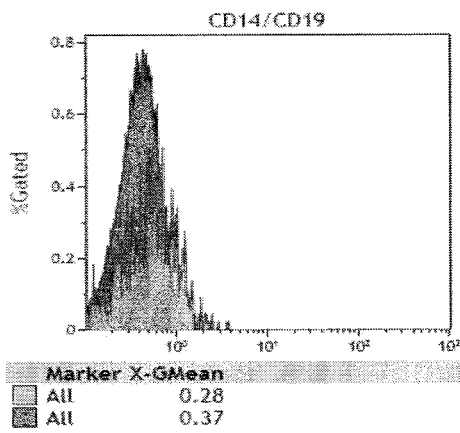
Figure 3L:
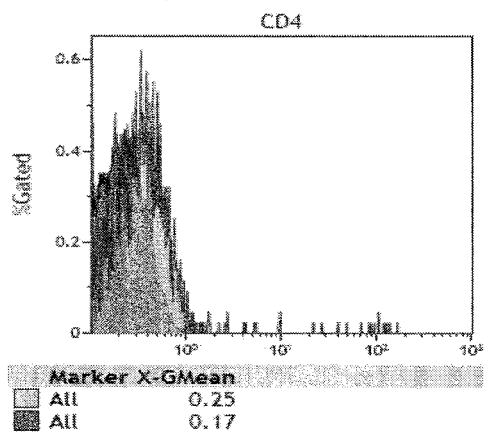
Figure 3M:
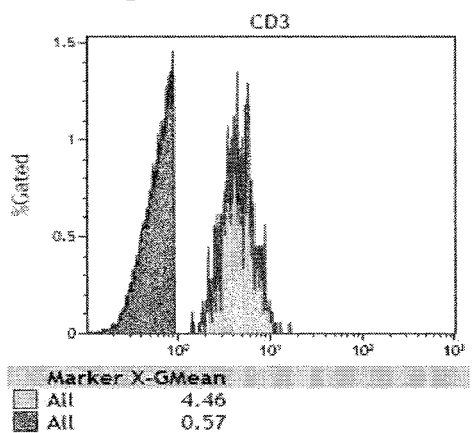
Figure 4A:
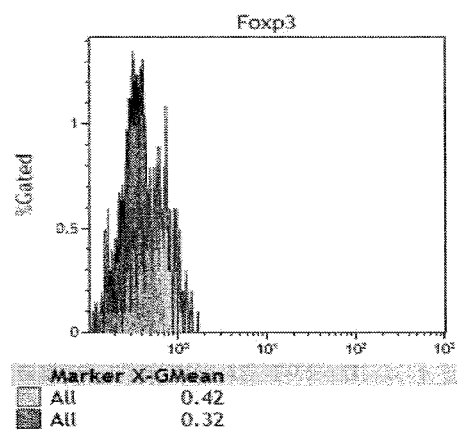
FIG. 4A-4L are histograms illustrating the expression of Foxp3 (FIG. 4A), CD25 (FIG. 4B), PD-1 (FIG. 4C), GITR (FIG. 4D), PI-16 (FIG. 4E), CD1d tetramer (FIG. 4F), TCR Vα24_Jα18 (FIG. 4G), CTLA-4 (FIG. 4H), LAP (FIG. 4I), IL-15Rα (FIG. 4J) CD4, CD14, CD16 and CD19 (FIG. 4K) and CD3 (FIG. 4L) of the enriched CD4$^-$CD14$^-$ CD16$^-$CD19$^-$CD25$^-$ cell fraction.
Figure 4B:
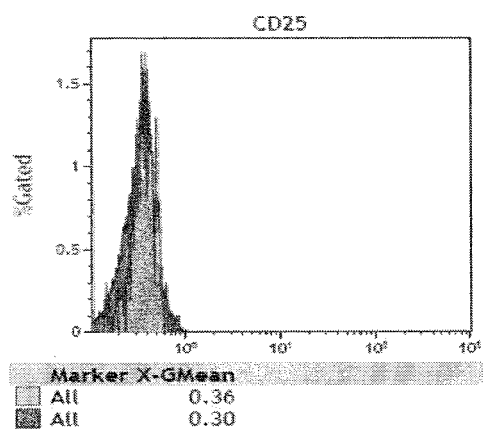
Figure 4C:
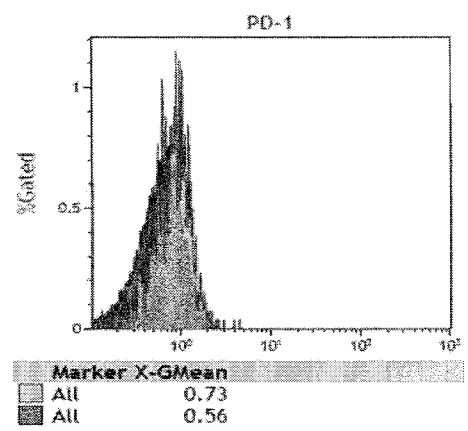
Figure 4D:
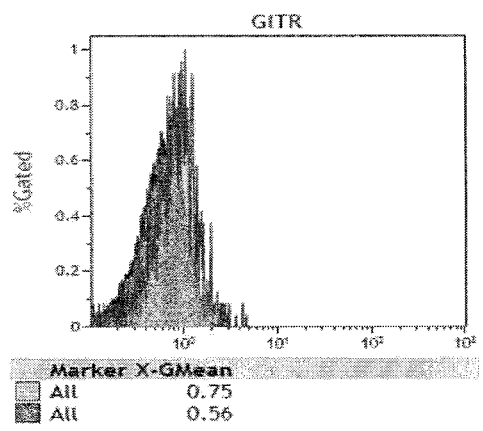
Figure 4E:
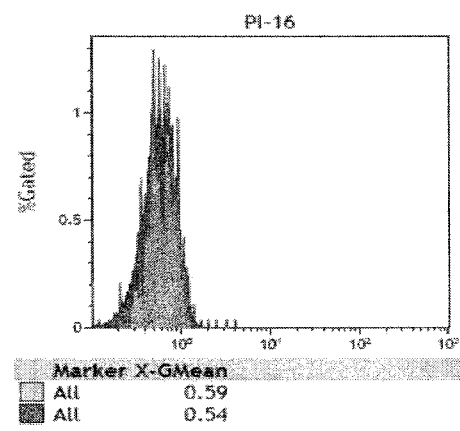
Figure 4F:
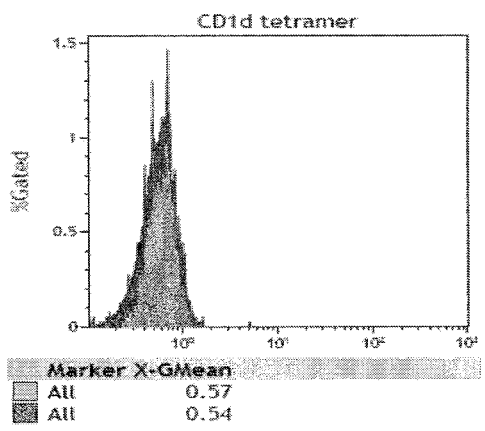
Figure 4G:
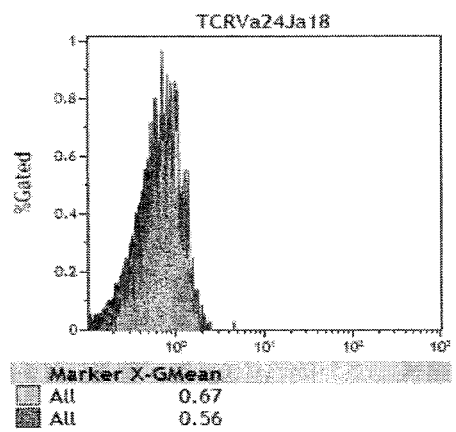
Figure 4H:
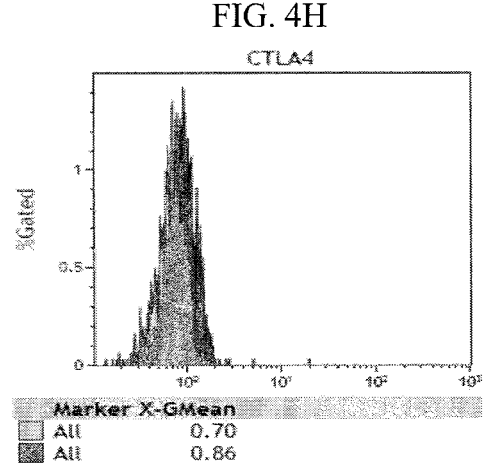
Figure 4I:
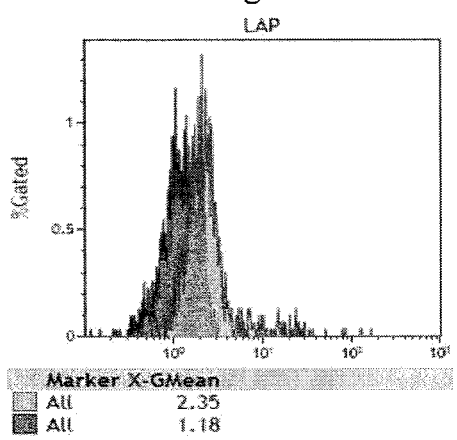
Figure 4J:
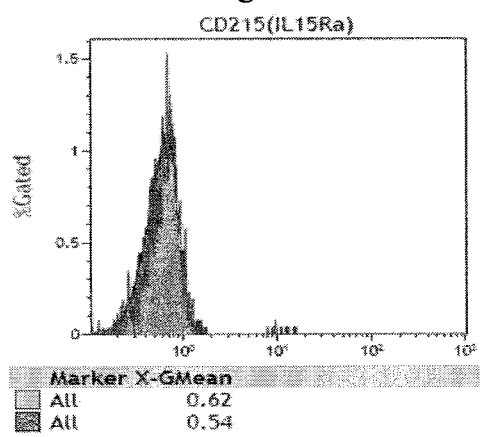
Figure 4K:
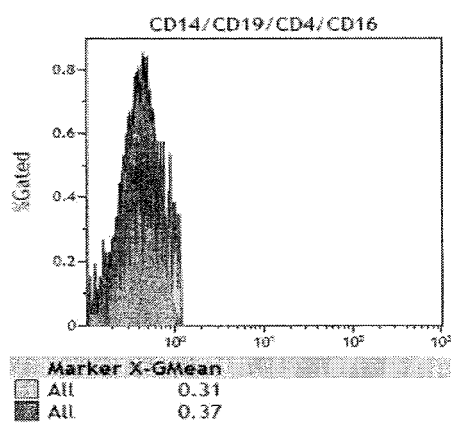
Figure 4L:
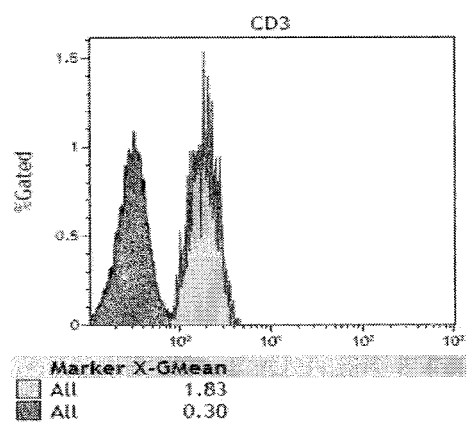
Figure 5A:
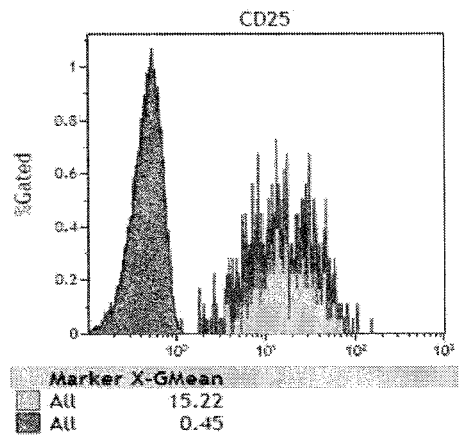
FIG. 5A-5M are histograms illustrating the expression of CD25 (FIG. 5A), PD-1 (FIG. 5B), GITR (FIG. 5C), PI-16 (FIG. 5D), CD1d tetramer (FIG. 5E), TCR Vα24_Jα18 (FIG. 5F), CTLA-4 (FIG. 5G), LAP (FIG. 5H), IL-15Rα (FIG. 5I), Foxp3 (FIG. 5J), CD14 and CD19 (FIG. 5K), CD4 (FIG. 5L) and CD3 (FIG. 5M) of the modified NKT cells in Example 2.
Figure 5B:
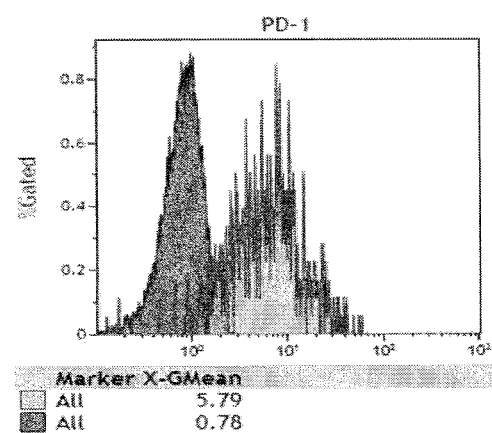
Figure 5C:
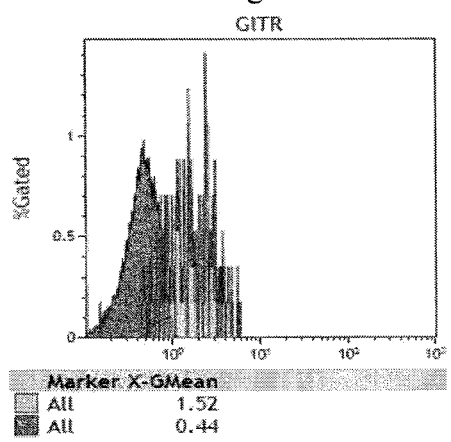
Figure 5D:
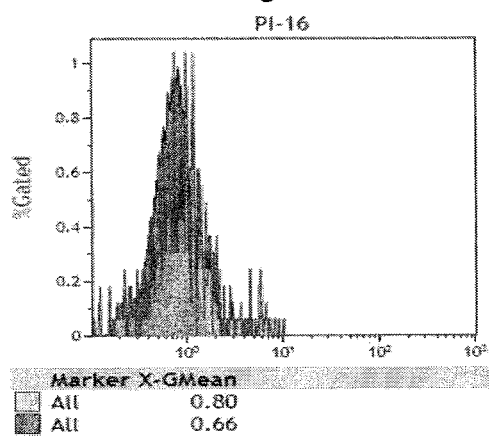
Figure 5E:
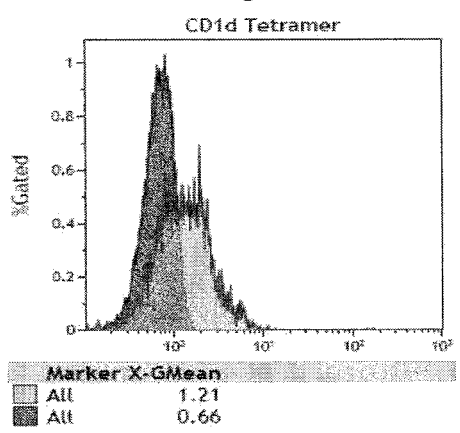
Figure 5F:
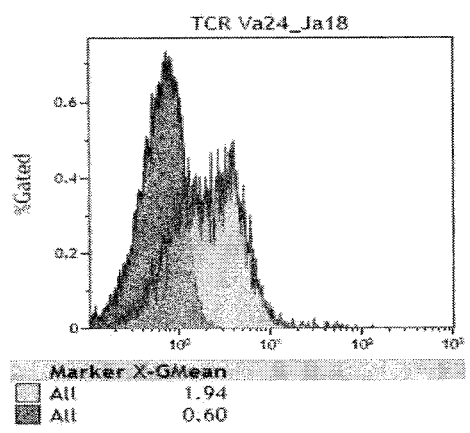
Figure 5G:
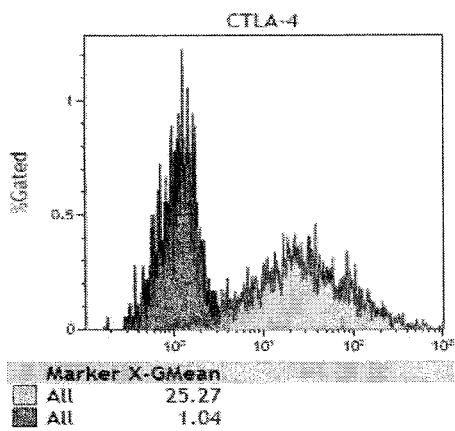
Figure 5H:
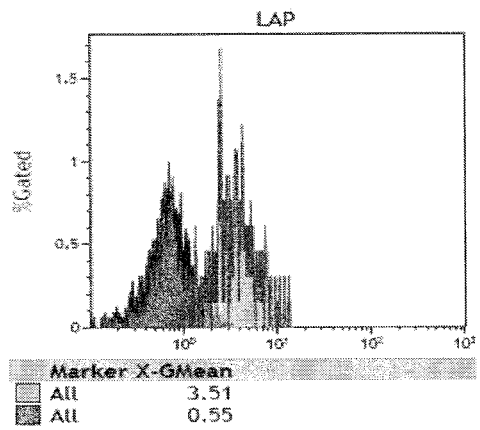
Figure 5I:
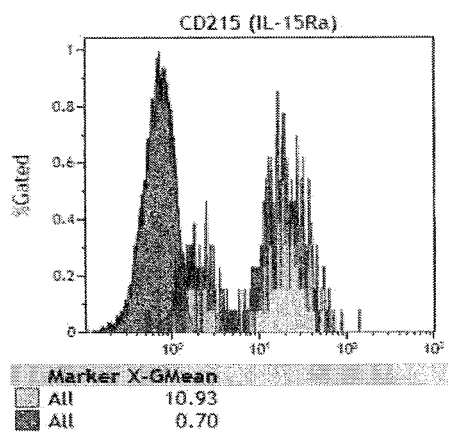
Figure 5J:
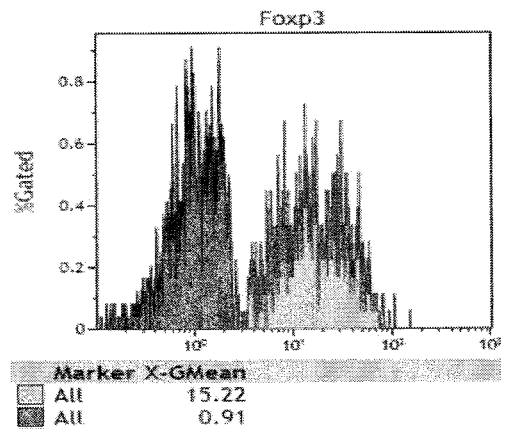
Figure 5K:
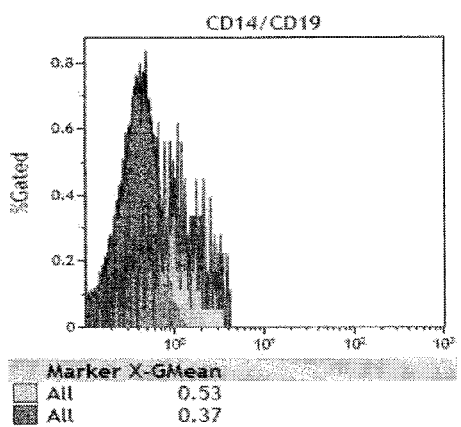
Figure 5L:
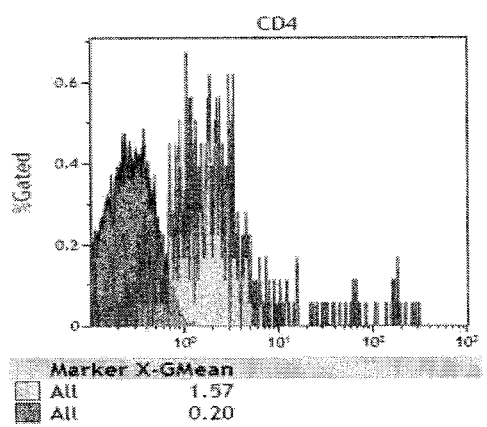
Figure 5M:
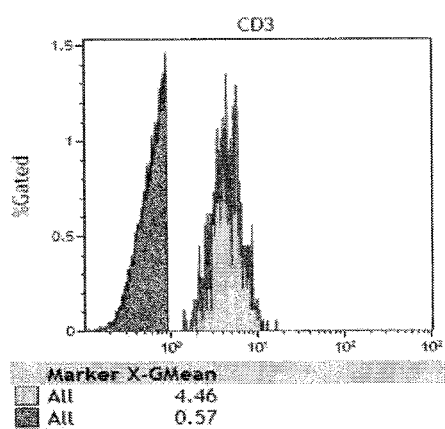
Figure 6G:
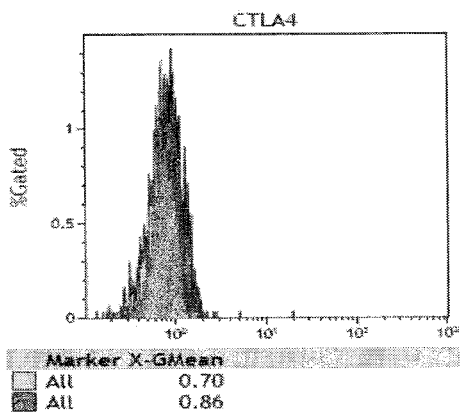
Figure 6H:
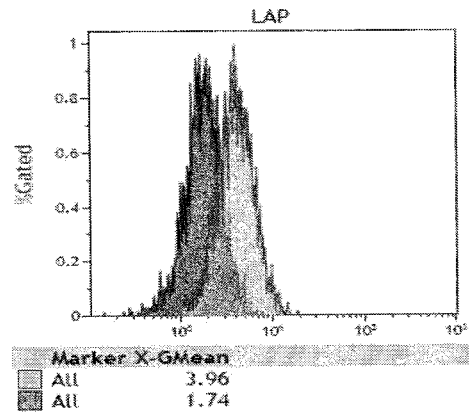
Figure 6I:
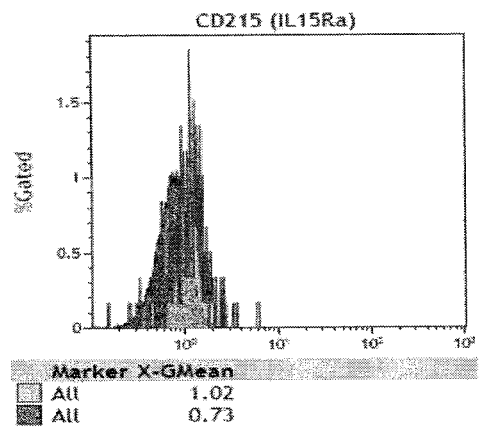
Figure 6J:
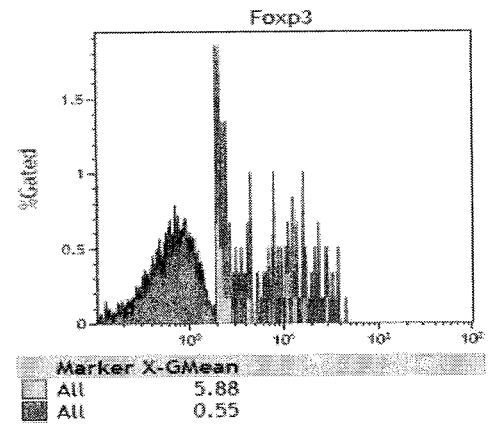
Figure 6K:
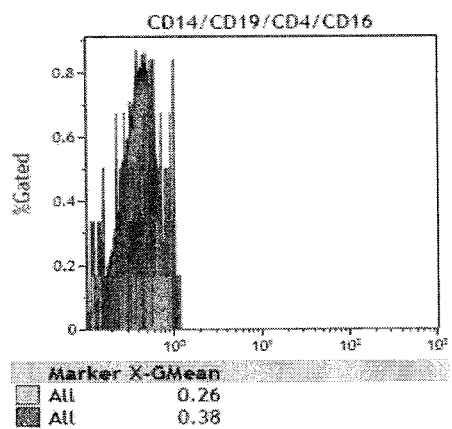
Figure 6L:
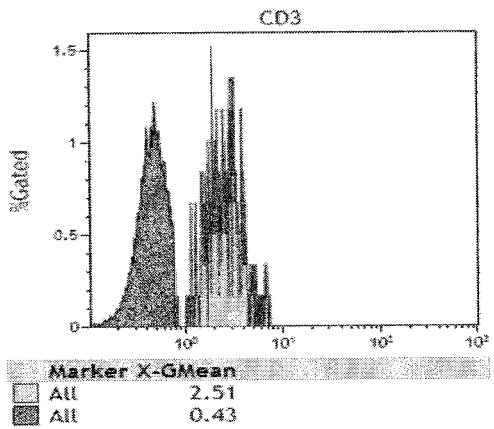

As shown in FIG. 2, the signal levels of CD4, CD14, CD16, CD19, and CD25 of the enriched $CD14^-/CD19^-/CD25^-$ cell fraction (FIG. 2D) and the enriched $CD4^-CD14^-CD16^-CD19^-CD25^-$ cell fraction (FIG. 2F) were much lower than those of the non-enriched cell fraction (FIG. 2B).

Example 2

In Vitro Culture of First Embodiment of Modified NKT Cells

As illustrated in FIG. 1B, the enriched $CD14^-CD19^-CD25^-$ cell fraction from Example 1 was cultured as follows:

(a) the enriched $CD14^-/CD19^-/CD25^-$ cell fraction was cultured with a composition comprising 3 ml of R-10 medium and 40 ng/ml TGF-β in 6-well plates previous coated with 1 µg of anti-human CD3 antibody (Biolegend, USA) on day 0.

(b) 40 ng/ml of IL-15 (BioLegend) was added to the culture in step (a) on Day 1.

(c) On day 3, half of the cultured cells in step (b) were harvested and span down, followed by re-suspending cell pellet with R-10 medium and 40 ng/ml of TGF-β in 6-well plates.

(d) 40 ng/ml of IL-15 (BioLegend) was added to the culture in step (c) on Day 4.

(e) On day 6, in the cultured cells, the cells carried $CD3^+CD56^+CD8^+$ $PD-1^+$phenotypes with at least one phenotype selected from $CD25^+$, $Foxp3^+$, $CTLA-4^+$and $LAP^+$were analyzed and referred as the modified NKT cells.

The modified NKT cells in step (e) were assayed for their phenotype using Gallios Flow Cytometer (Beckman Coulter, Inc.), Kazula software version 1.2 (Beckman Coulter, Inc.) and antibodies listed in Table 2.

TABLE 2

Antibodies used for modified NKT cells phenotype

1. Anti-Human CD56-APC-Alexa Fluor 700, Anti-human CD56-PE-Cy7 (Biolegend)
2. Anti-Human CD19-APC-Alexa Fluor750 (Beckman Coulter Inc.)
3. Anti-Human CD14-APC-Alexa Fluor750 (Beckman Coulter Inc.)
4. Anti-Human CD4-PE-Cy7; Anti-human CD4-A750 (Beckman Coulter Inc.)
5. Anti-Human Foxp3-APC (eBioscience, USA)
6. Mouse IgG1, κ Isotype Ctrl APC (eBioscience)
7. Anti-Human CD3-Krome Orange, Anti-Human CD3-APC Alexa Fluor750 (Beckman Coulter Inc.)
8. Anti-Human CD8-Pacific Blue (Biolegend), Anti-human APC-CD8a (Biolegend)
9. Anti-Human CD25-FITC, Anti-Human CD25-PE (Biolegend) Anti-human CD25-A700 (Beckman)
11. Anti-Human PD-1 PerCP-Cy5.5 (Biolegend)
12. Anti-Human GITR Alexa 488 (eBioscience)
13. Anti-Human PI-16 PE, Anti-human CD16-A750 (BDBioscience)
14. Anti-human CD215 (IL-15R$_α$) PE (Biolegend)
15. PE labeled human CD1d tetramer loaded a-Galcer (ProImmune Ltd, UK)
16. Anti-Human CTLA-4 PE (Biolegend)
17. Anti-Human LAP PE (Biolegend)
18. Anti-human TCR Vα24-Jα18 (iNKT cell) PerCP/Cy5.5 (Biolegend)
19. Anti-human CD122 (IL-2 R$_β$) PE-Cy7 (Biolegend)

In this working example, the expression level of the cell surface marker using FACS/flow cytometry analysis are defined in Table 3. The interpretation for the expression levels in Table 3 is an example of defining the expression level of the cell surface marker. It should be noted that the flow cytometry signal level intensity varies with the following factors: the flow cytometry, the software and different batches of antibody used.

TABLE 3

| Symbol | Interpretation |
|---|---|
| − | the cellular marker is not detectably present in fluorescence activated cell sorting over an isotype control (i.e., net MFI of the surface marker is less than about 1.5) |
| + | the cellular surface marker is detectably present in fluorescence activated cell sorting over an isotype control (i.e., net MFI of the surface marker is greater than or equal to about 1.5) |

Results:

As shown in FIG. 3A-3M, the mononuclear cells of the enriched $CD14^-CD19^-CD25^-$ cell fraction have the phenotype of $CD14^-CD19^-$ $CD3^+CD56^+CD8^+CD4^-CD25^-$ $Foxp3^-PD-1^-CTLA-4^-GITR^-$ $PI-16^-CD1d$ $tetramer^-LAP^-$ TCR $Vα24\_Jα18^-IL-15Rα^-$.

FIG. 5A-5M illustrate the phenotype of the modified NKT cells in Example 2 is $CD14^-CD19^-CD3^+CD56^+CD8^+CD4^-CD25^+Foxp3^+PD-1^+CTLA-4^+GITR^-PI-16^-CD1d$ $tetramer^-LAP^+TCR$ $Vα24\_Jα18^-$ $IL-15Rα^+$ phenotype.

Table 4 shows the net MFI of the mononuclear cells of the enriched $CD14^-$ $CD19^-CD25^-$ cell fraction and the modified NKT cells cultured therefrom.

TABLE 4

|  | Enriched CD14⁻CD19⁻ CD25⁻ Cell Fraction | Modified NKT |
|---|---|---|
| CD14 | −0.09 | 0.16 |
| CD19 | −0.09 | 0.16 |
| CD4 | 0.08 | 1.37 |
| CD16 | Not tested | Not tested |
| CD3 | 3.12 | 3.89 |
| CD56 | 14.32 | 12.8 |
| CD8 | 13.06 | 8.89 |
| CD25 | 0.11 | 14.77 |
| Foxp3 | −0.23 | 14.31 |
| PD-1 | 0.61 | 5.01 |
| CTLA-4 | −0.33 | 24.23 |
| GITR | 0.1 | 1.08 |
| PI-16 | −0.02 | 0.14 |
| CD1d tetramer | 0.1 | 0.55 |
| LAP | −0.01 | 2.96 |
| TCR Vα24_Jα18 | 0.01 | 1.34 |
| IL-15Rα | 0.04 | 10.23 |

Based on the results of FIGS. 5A, 5B, 5D, 5E, 5F, 5J, 5K, and 5M, only one exclusive cell population could be identified. Thus, current invention show that "the CD3$^+$CD56$^+$CD8$^+$ NKT cell population analyzed in the step (e) of Example 2 (modified NKT cells) carry CD25$^+$ PD-1$^+$ PI-16$^-$ CD1d tetramer$^-$ TCR Vα24_Jα18$^-$ Foxp3$^+$ CD14$^-$ CD19$^-$ CD3$^+$phenotypes." The differences between the enriched CD14$^-$ CD19$^-$ CD25$^-$ mononuclear cell phenotype and modified NKT cell phenotype are outlined below.

Enriched CD14$^-$CD19$^-$CD25$^-$mononuclear cells have a phenotype Foxp3$^-$CD25$^-$PD-1$^-$CTLA-4$^-$LAP$^-$IL-15Rα$^-$, whereas the modified NKT cells have phenotype Foxp3$^+$CD25$^+$PD-1$^+$CTLA-4$^+$ LAP$^-$IL-15Rα$^+$.

The expression of Foxp3 is upregulated in modified NKT cells by at least 62 times compare to that of Enriched CD14$^-$CD19$^-$CD25$^-$ Cells.

The expression of CD25 is upregulated in modified NKT cells by at least 130 times compare to that of Enriched CD14$^-$CD19$^-$CD25$^-$ Cells.

The expression of PD-1 is upregulated in modified NKT cells by at least 8.5 times compare to that of Enriched CD14$^-$CD19$^-$CD25$^-$ Cells.

The expression of CTLA-4 is upregulated in modified NKT cells by at least 73 times compare to that of Enriched CD14$^-$CD19$^-$CD25$^-$ Cells.

The expression of IL-15Rα is upregulated in modified NKT cells by at least 250 times compare to that of Enriched CD14$^-$CD19$^-$CD25$^-$ Cells.

Example 3

In Vitro Culture of Second Embodiment of Modified NKT Cells

Figure 1C:
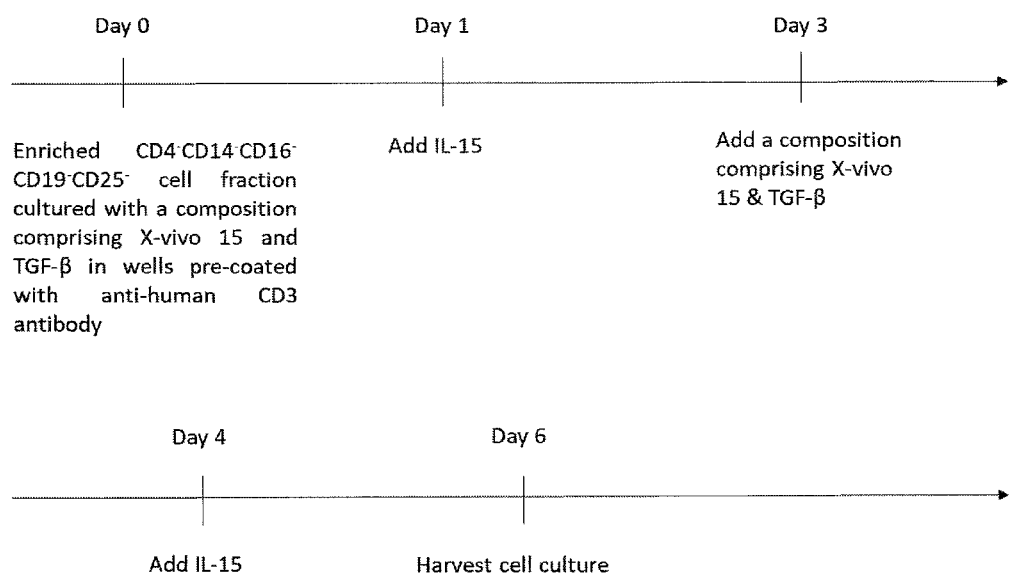

As illustrated in FIG. 1C, the enriched CD4$^-$CD14$^-$CD16$^-$CD19$^-$CD25$^-$ cell fraction from Example 1 was cultured as follows:

(a) the enriched CD4$^-$CD14$^-$CD16$^-$CD19$^-$CD25$^-$ cell fraction was cultured with a composition comprising 3 ml of X-Vivo 15 and 40 ng/ml TGF-β in 6-well plates previous coated with 1 μg of anti-human CD3 antibody (Biolegend) on day 0.

(b) 80 ng/ml of IL-15 (BioLegend) was added to the culture in step (a) on Day 1.

(c) On day 3, half of cultured cells in step (b) were harvested and span down, followed by re-suspending cell pellet with 3 ml X-Vivo 15 and 40 ng/ml of TGF-β in 6-well plates.

(d) 80 ng/ml of IL-15 (BioLegend) was added to the culture in step (c) on Day 4.

(e) On day 6, in the cultured cells, the cells carried CD3$^+$CD56$^+$CD8$^+$ PD-1$^+$phenotypes with at least one phenotype selected from CD25$^+$, Foxp3$^+$, CTLA-+ and LAP$^+$ were analyzed in Example 3 and referred as the modified NKT cells.

The modified NKT cells in step (e) were assayed for their phenotype according to the protocol in Example 2.

Results:

As shown in FIG. 4A-4L, the mononuclear cells of the enriched CD4$^-$CD14$^-$CD16$^-$CD19$^-$CD25$^-$ cell fraction have the phenotype of CD14$^-$CD19$^-$ CD3$^+$CD16$^-$CD56$^+$CD8$^+$CD4$^-$CD25$^-$Foxp3$^-$PD-1$^-$CTLA-4$^-$GITR$^-$PI-16$^-$ CD1d tetramer$^-$ LAP$^-$TCR Vα24_Jα18$^-$IL-15Rα$^-$.

FIG. 6A-6L illustrate the phenotype of the modified NKT cells in Example 3 is CD14$^-$CD19$^-$CD3$^+$CD16$^-$CD56$^+$CD8$^+$CD4$^-$CD25$^+$Foxp3$^+$PD-1$^+$CTLA-4$^+$GITR$^-$PI-16$^-$ CD1d tetramer$^-$LAP$^+$TCR Vα24_Jα18$^-$ LAP$^+$IL-15Rα$^-$ phenotype.

Table 5 shows the net MFI of the enriched CD4$^-$CD14$^-$CD16$^-$CD19$^-$CD25$^-$ mononuclear cells and the modified NKT cells cultured therefrom.

TABLE 5

|  | Enriched CD4⁻CD14⁻ CD16⁻ CD19⁻CD25⁻ Cell Fraction | Modified NKT |
|---|---|---|
| CD14 | −0.06 | −0.12 |
| CD19 | −0.06 | −0.12 |
| CD4 | −0.06 | −0.12 |
| CD16 | −0.06 | −0.12 |
| CD3 | 1.53 | 2.08 |
| CD56 | 3.24 | 2.99 |
| CD8 | 5.99 | 11.76 |
| CD25 | 0.06 | 5.14 |
| Foxp3 | 0.1 | 5.33 |
| PD-1 | 0.17 | 2.6 |
| CTLA-4 | −0.16 | 14.63 |
| GITR | 0.19 | 0.96 |
| PI-16 | 0.05 | 0.25 |
| CD1d tetramer | 0.03 | 0.21 |
| LAP | 1.17 | 2.22 |
| TCR Vα24_Jα18 | 0.11 | 0.57 |
| IL-15-Rα | 0.08 | 0.29 |

Based on the results of FIGS. 6A, 6B, 6D, 6E, 6F, 6G, 6I, 6J, 6K, and 6L, only one exclusive cell population could be identified. Thus, current invention show that "the CD3$^+$CD56$^+$ CD8$^+$ NKT cell population analyzed or isolated from the step (e) of Example 3 (modified NKT cells) carry CD25$^+$ PD-1$^+$ PI-16− CD1d tetramer- TCR Vα24_Jα18$^-$ CTLA-4$^+$ IL-15-Rα$^-$ Foxp3$^+$ CD14$^-$ CD19$^-$ CD4$^-$ CD16$^-$ CD3$^+$ phenotypes." The differences between the enriched CD4$^-$CD14$^-$ CD16$^-$ CD19$^-$ CD25$^-$ mononuclear cell phenotype and modified NKT cell phenotype are outlined below.

Enriched CD14$^-$CD19$^-$ CD25$^-$ mononuclear cells have a phenotype Foxp3$^-$CD25$^-$ PD-1$^-$CTLA-4$^-$LAP$^-$, whereas the modified NKT cells have phenotype Foxp3$^+$CD25$^+$ PD-1 CTLA-4$^+$ LAP$^+$.

The expression of Foxp3 is upregulated in modified NKT cells by at least 53 times compare to that of Enriched CD14$^-$CD19$^-$CD25$^-$ Cells.

The expression of CD25 is upregulated in modified NKT cells by at least 85 times compare to that of Enriched CD14$^-$CD19$^-$CD25$^-$ Cells.

The expression of PD-1 is upregulated in modified NKT cells by at least 15 times compare to that of Enriched CD14$^-$CD19$^-$CD25$^-$ Cells.

The expression of CTLA-4 is upregulated in modified NKT cells by at least 90 times compare to that of Enriched CD14⁻CD19⁻CD25⁻ Cells.

Example 4

The Effect of IL-15 Concentration on Modified NKT Cell Culture

An in vitro evaluation of the concentration of IL-15 on modified NKT cell culture was performed using FACS/Flow cytometry.

The following IL-15 concentrations were used to generate modified NKT cells of Example 2: 5 ng/ml IL-12, 10 ng/ml, 20 ng/ml, 40 ng/ml, 80 ng/ml and 160 ng/ml. Results: The expression levels of Foxp3, CD25, CTLA-4 and PD-1 are higher when IL-15 concentration is between about 20 ng/ml to about 160 ng/ml.

Example 5

Functional Assessment of Modified NKT Cell Suppressive Capacity Toward the Proliferation of Activated CFSE-Labelled T Lymphocytes "T Lymphocyte Responder Cell" assay: carboxyfluorescein diacetate succinimidyl ester (CFSE)-labelled CD25⁻ peripheral blood mononuclear cells (CD25⁻ PBMC) were stimulated with 3 ug/ml anti-CD3 and 1 ug/ml anti-CD28 antibodies to activate CFSE-labelled T lymphocyte responder cells. The modified NKT cells in Example 2 and Example 3 were added to the CFSE-labelled T lymphocyte responder cells to assess the immunosuppressive property. After 4 days of co-culture, CFSE fluorescence dilution was measured.

Figure 7A:
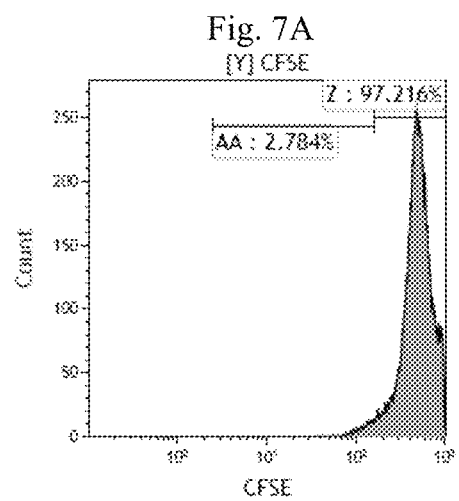
FIG. 7A-7C are histogram plots of CFSE fluorescence of T lymphocytes illustrating the suppressive effect of the modified NKT cells in Example 2 (cultured from enriched CD14$^-$CD19$^-$CD25$^-$ cell fraction) on T lymphocyte proliferation.
Figure 7B:
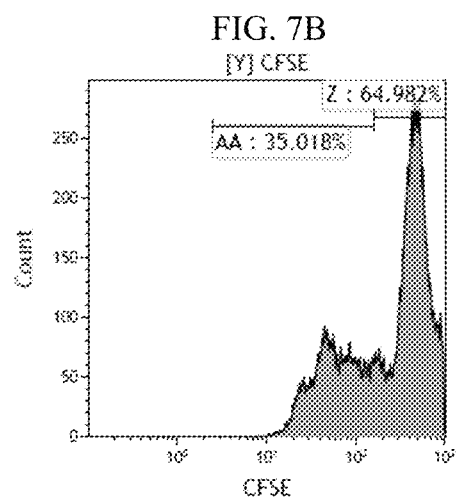
Figure 7C:
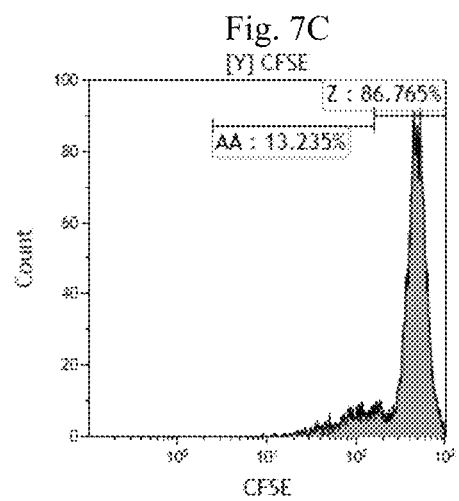

Results for modified NKT cells in Example 2: FIG. 7A illustrates the CFSE dilution analysis of CFSE-labelled T lymphocyte responder cell without any antibody stimulation (2.78%). The addition of anti-CD3 antibody and anti-CD28 antibody induced the proliferation of CF SE-labelled T lymphocyte responder cells (35.02%), as illustrated in FIG. 7B. FIG. 7C shows the addition of modified NKT cell in Example 2 to the CFSE-labelled T lymphocyte responder cells reduced the proliferation of CFSE-labelled T lymphocyte responder cells from 35.02% to 13.24% (a 62% reduction).

Figure 8A:
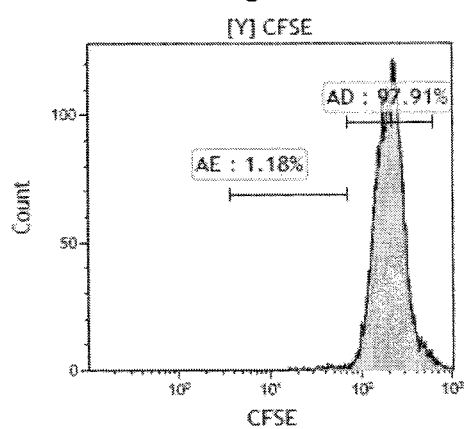
FIG. 8A-8C are histogram plots of CFSE fluorescence of T lymphocytes illustrating the suppressive effect of the modified NKT cells in Example 3 (cultured from enriched CD4$^-$CD14$^-$CD16$^-$CD19$^-$CD25$^-$ cell fraction) on T lymphocyte proliferation.
Figure 8B:
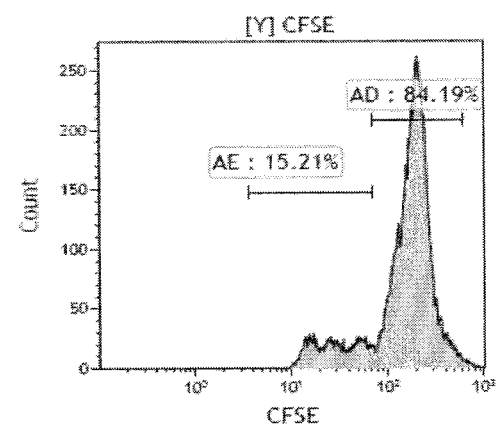
Figure 8C:
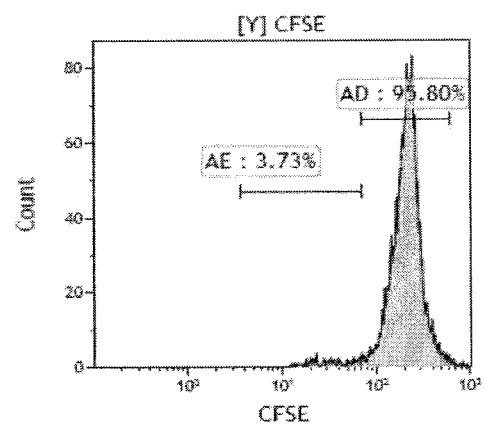

Results for modified NKT cells in Example 3: FIG. 8A illustrates the CFSE dilution analysis of CFSE-labelled T lymphocyte responder cell without any antibody stimulation (1.18%). The addition of anti-CD3 antibody and anti-CD28 antibody induced the proliferation of CFSE-labelled T lymphocyte responder cells (15.21%), as illustrated in FIG. 8B. FIG. 8C shows the addition of modified NKT cell in Example 3 to the CFSE-labelled T lymphocyte responder cells reduced the proliferation of CFSE-labelled T lymphocyte responder cells from 15.21% to 3.7% (a 75.5% reduction).

These results show that the modified NKT cell of the present invention is effective in suppressing the proliferation of activated CF SE-labelled T lymphocytes, which is a key player in autoimmune diseases.

Example 6

The Effect of IL-2 on the Generation of Modified NKT Cells

An in vitro evaluation of the effect of IL-2 on modified NKT cell culture was performed using FACS/Flow cytometry. The enriched CD14⁻CD19⁻CD25⁻ mononuclear cells of Example 1 were cultured with (a) anti-CD3 antibody+ TGF-β+IL-2 or (b) anti-CD3 antibody+TGF-β+IL-15 in according to the steps in Example 2.

TABLE 6

The % of modified NKT cell generated with different culture mediums or growth factors

| Type of growth factors | CD3 Ab + TGF-β + IL-2 (IL-2) | CD3 Ab + TGF-β + IL-15 (IL-15) | IL15/IL-2 (% increase) |
|---|---|---|---|
| Percentage of modified NKT cells generated | 1.26 | 15.47 | 1127.78 |

As shown in Table 6, the % of an exemplary embodiment of the modified NKT cells generated with TGF-β and IL-2 is 1.26. On the other hand, the % of the modified NKT cells generated with TGF-β and IL-15 is 15.47, this represents a 11 times increase compare to the % of the modified NKT cells generated with TGF-β and IL-2.

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. A population of natural killer T (NKT) cells carrying a phenotype of CD3⁺CD56⁺CD8⁺CD1d tetramer⁻TCR Vα24_Jα18⁻PD-1⁺CD25⁺Foxp3⁺CTLA-4⁺LAP⁺GITR⁻ and PI-16⁻.

2. The population of natural killer T cells of claim 1, wherein the NKT cells further comprise the IL-Rα⁺phenotype.

3. A composition, comprising
   (a) a population of natural killer T cells carrying a phenotype of CD3⁺CD56⁺CD8⁺CD1d tetramer⁻TCR Vα24_Jα18⁻PD-1⁺CD25⁺Foxp3⁺CTLA-4⁺LAP⁺ GITR⁻and PI-16⁻; and
   (b) a pharmaceutically acceptable carrier or excipient.

4. The composition of claim 3, wherein the NKT cells further comprise the IL-15Rα⁺phenotype.

5. The composition of claim 3, wherein the NKT cells further comprise the IL-15Rα⁻phenotype.

6. A method of generating the population of natural killer T cells of claim 1, comprising the steps of
   (a) culturing an enriched CD14⁻CD19⁻CD25⁻mononuclear cell fraction or an enriched CD4⁻CD14⁻CD16⁻CD19⁻CD25⁻mononuclear cell fraction with transforming growth factor beta (TGF-β), anti-CD3 antibody, and cell culture medium;
   (b) contacting the cultured cell fraction from step (a) with IL-15;
   (c) contacting the cultured cell fraction from step (b) with transforming growth factor beta (TGF-β);

(d) contacting the cultured cell fraction from step (c) with IL-15; and (e) isolating the population of modified natural killer T cells carrying a phenotype of $CD3^+CD56^+CD8^+CD1d$ tetramer$^-$TCR $V\alpha24\_J\alpha18^-$PD-1$^+$CD25$^+$Foxp3$^+$ CTLA-4$^+$LAP$^+$GITR$^-$and PI-16$^-$.

7. The method of claim 6, wherein the cell culture medium comprises a mammalian cell culture medium and a media supplement.

8. The method of claim 7, wherein the mammalian cell culture medium is RPMI medium 1640 and the media supplement is fetal bovine serum.

9. The method of claim 6, wherein the cell culture medium is a hematopoietic cell medium.

10. The method of claim 6, wherein the NKT cells further comprise the IL-R$\alpha^+$phenotype.

11. The method of claim 6, wherein the contact time of the enriched cell fraction with the transforming growth factor beta (TGF-$\beta$) or IL-15 is about 1 day to about 9 days.

12. A population of natural killer T (NKT) cells carrying a phenotype of $CD3^+CD56^+CD8^+CD1$ d-tetramer$^-$TCR $V\alpha24\_J\alpha18^-$GITR$^-$PI-16$^-$CD25$^+$Foxp3$^+$CTLA-4$^+$LAP$^+$ PD-1$^+$IL-15R$\alpha^-$.

13. The method of claim 6, wherein the NKT cells further comprise the IL-15R$\alpha$- phenotype.

14. The method of claim 6, in step (b) or (d), the concentration of IL-15 is 20 ng/ml to 160 ng/ml.

* * * * *